(12) United States Patent
Amir et al.

(10) Patent No.: US 9,717,922 B2
(45) Date of Patent: Aug. 1, 2017

(54) WIRELESS RECHARGING SYSTEM AND METHOD FOR FLEXIBLE IMPLANTABLE SUBCUTANEOUS MEDICAL DEVICE

(71) Applicant: NewPace Ltd., Caesarea (IL)

(72) Inventors: Jack Amir, Mazkeret Batya (IL); Moty Mocha, Beit Dagan (IL); Gera Strommer, Haifa (IL); James Kelley, Coon Rapids, MN (US); Avraham Broder, Petach Tikva (IL)

(73) Assignee: NewPace Ltd., Caesarea (IL)

( * ) Notice: Subject to any disclaimer, the term of this patent is extended or adjusted under 35 U.S.C. 154(b) by 0 days.

(21) Appl. No.: 14/976,501

(22) Filed: Dec. 21, 2015

(65) Prior Publication Data

US 2016/0175600 A1    Jun. 23, 2016

Related U.S. Application Data

(60) Provisional application No. 62/095,080, filed on Dec. 22, 2014.

(51) Int. Cl.
*A61N 1/375* (2006.01)
*A61N 1/378* (2006.01)
(Continued)

(52) U.S. Cl.
CPC ......... *A61N 1/3787* (2013.01); *A61N 1/0563* (2013.01); *A61N 1/36125* (2013.01);
(Continued)

(58) Field of Classification Search
CPC ........................................ A61N 1/375–1/3758
See application file for complete search history.

(56) References Cited

U.S. PATENT DOCUMENTS

| | | | | | |
|---|---|---|---|---|---|
| 4,495,917 | A | * | 1/1985 | Byers | A61B 5/0031 128/903 |
| 4,979,506 | A | * | 12/1990 | Silvian | A61N 1/3727 128/903 |

(Continued)

FOREIGN PATENT DOCUMENTS

WO    2016038599 A1    3/2016

OTHER PUBLICATIONS

Partial European Search Report Mailed Jun. 1, 2016 for European Application No. 15003630.9 (7 Pages).

*Primary Examiner* — Kennedy Schaetzle
(74) *Attorney, Agent, or Firm* — Brown Rudnick LLP

(57) ABSTRACT

Flexible subcutaneous implantable medical device (IMD), including an elongated and flexible body (256), a plurality of electronic components, at least one rechargeable battery (426), at least one antenna (260, 422), at least one lead (254) and at least one transition unit (252), the antenna for receiving and transmitting electromagnetic radiation and the lead for providing an electric shock, wherein the elongated and flexible body is structured from a plurality of units, wherein a first one of the plurality of units encapsulates the rechargeable battery, wherein each one of the other plurality of units respectively encapsulates a respective one of the plurality of electronic components, wherein the antenna is positioned in the transition unit, wherein the transition unit is covered with a biocompatible polymer, wherein the antenna receives electromagnetic radiation for recharging the rechargeable battery and wherein the antenna includes a copper coil having a generally cylindrical shape.

21 Claims, 5 Drawing Sheets

(51) Int. Cl.
*H02J 7/02* (2016.01)
*H02J 7/04* (2006.01)
*A61N 1/372* (2006.01)
*A61N 1/39* (2006.01)
*A61N 1/36* (2006.01)
*A61N 1/05* (2006.01)
*A61B 5/0205* (2006.01)

(52) U.S. Cl.
CPC ....... *A61N 1/36189* (2013.01); *A61N 1/3758* (2013.01); *A61N 1/37229* (2013.01); *A61N 1/3956* (2013.01); *A61N 1/3968* (2013.01); *A61N 1/3975* (2013.01); *H02J 7/025* (2013.01); *H02J 7/04* (2013.01); *A61B 5/02055* (2013.01); *A61N 1/056* (2013.01)

(56) References Cited

U.S. PATENT DOCUMENTS

| | | | |
|---|---|---|---|
| 5,645,586 A | 7/1997 | Meltzer | |
| 6,950,705 B2 * | 9/2005 | Bardy | A61N 1/375 607/36 |
| 7,120,495 B2 * | 10/2006 | Bardy | A61N 1/375 607/36 |
| 7,363,082 B2 * | 4/2008 | Ransbury | A61N 1/375 607/116 |
| 7,522,574 B2 * | 4/2009 | Biagioni | H04W 76/002 370/310 |
| 7,894,915 B1 | 2/2011 | Chitre et al. | |
| 8,644,935 B2 * | 2/2014 | Leigh | A61N 1/375 174/50.5 |
| 9,480,846 B2 * | 11/2016 | Strother | A61N 1/08 |
| 2005/0021100 A1 * | 1/2005 | Tsukamoto | A61N 1/3787 607/29 |
| 2006/0206163 A1 * | 9/2006 | Wahlstrand | A61N 1/0502 607/46 |
| 2006/0247688 A1 | 11/2006 | Olson et al. | |
| 2008/0312725 A1 | 12/2008 | Penner | |
| 2010/0076524 A1 | 3/2010 | Forsberg et al. | |
| 2011/0004278 A1 | 1/2011 | Aghassian et al. | |
| 2012/0032522 A1 | 2/2012 | Schatz et al. | |
| 2013/0072747 A1 * | 3/2013 | Mashiach | A61N 1/0551 600/13 |
| 2015/0343228 A1 | 12/2015 | Strommer et al. | |

* cited by examiner

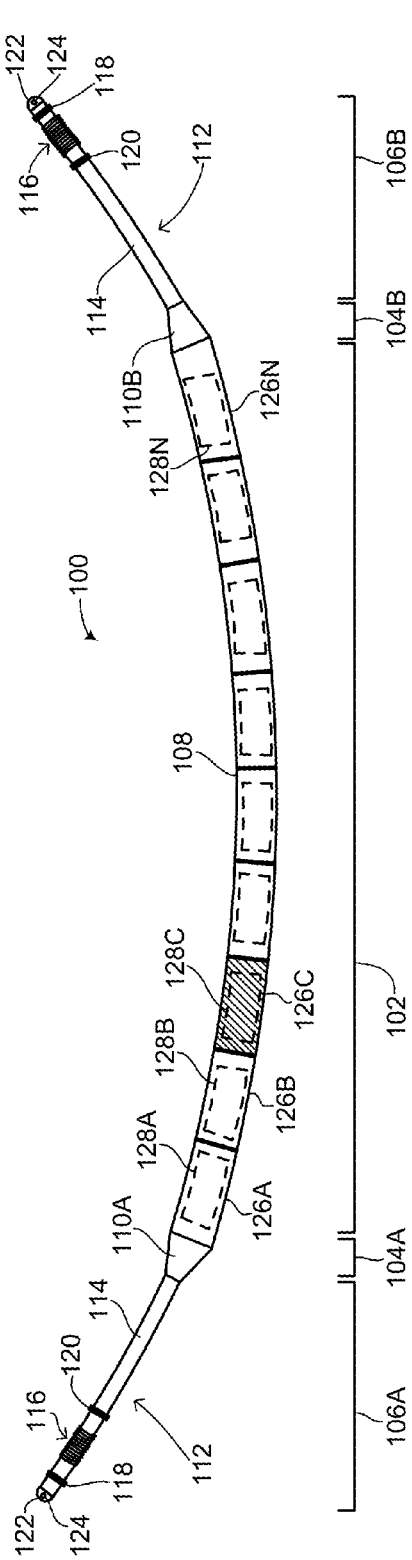
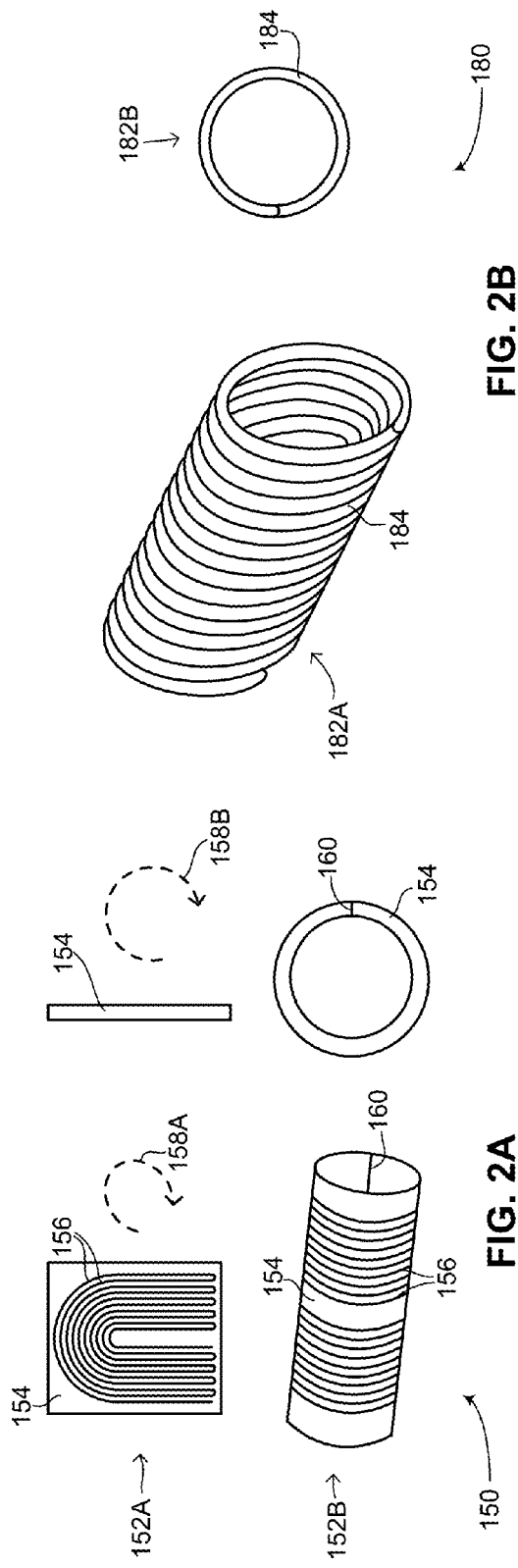
FIG. 1
FIG. 2A
FIG. 2B

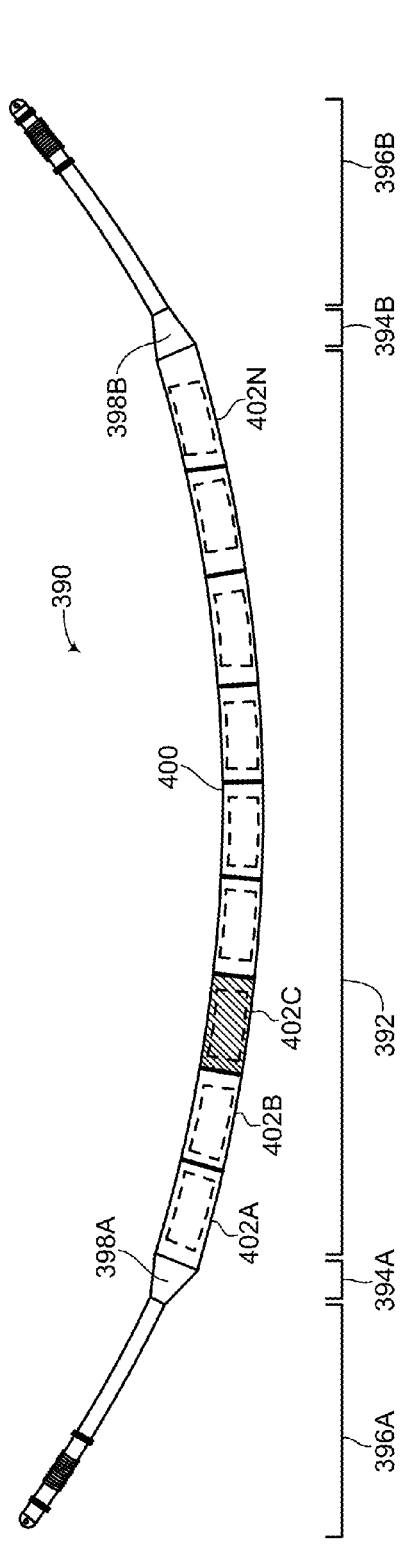
FIG. 5
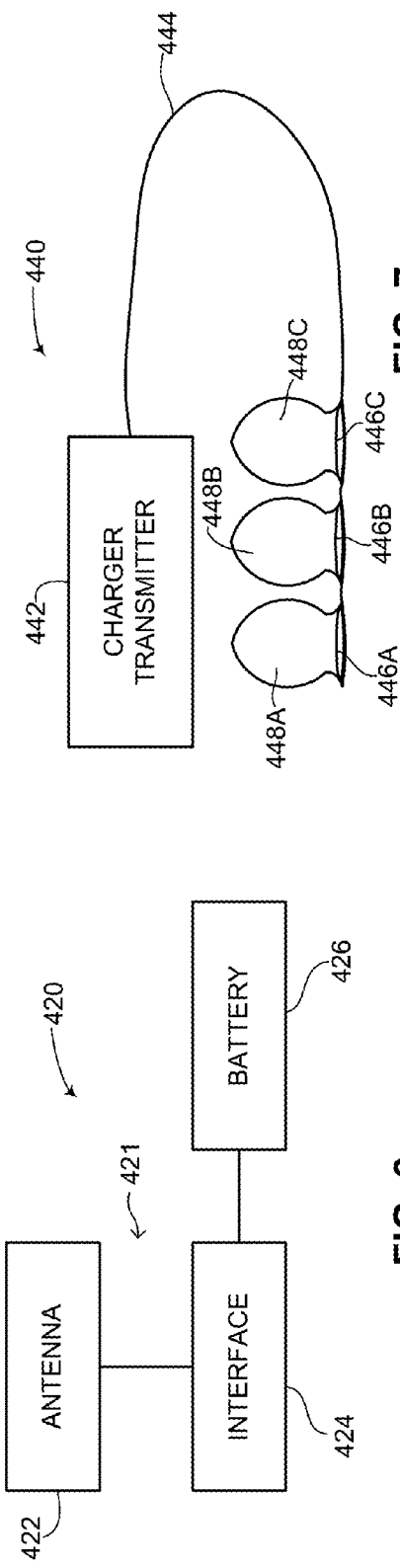
FIG. 7
FIG. 6

WIRELESS RECHARGING SYSTEM AND METHOD FOR FLEXIBLE IMPLANTABLE SUBCUTANEOUS MEDICAL DEVICE

RELATED APPLICATIONS

This claims priority to and the benefit of U.S. Provisional Patent Application Ser. No. 62/095,080, filed Dec. 22, 2014.

FIELD OF THE DISCLOSED TECHNIQUE

The disclosed technique relates to rechargeable subcutaneous medical devices, in general, and to methods and systems for wirelessly recharging such devices, in particular.

BACKGROUND OF THE DISCLOSED TECHNIQUE

Implantable medical devices (herein abbreviated IMD) are used by the medical industry for delivering various treatments to different kinds of medical conditions, whether they be heart conditions, gastrointestinal conditions or nervous system and brain conditions. Most IMDs require a source of power, either to operate the device, provide electrical stimulation to a part of the body as part of a treatment or therapy, or both. Since IMDs are implanted, various types of surgeries are required to insert the IMDs into a patient. These surgeries might be fully or minimally invasive however a surgery of sorts is required for placing the IMD inside the patient. Most state of the art IMDs employ a battery, which depending on the type of IMD and the kind of condition it is supposed to treat, may keep the IMD functioning for a number of years. For example, known intracardiac devices (herein abbreviated ICDs) such as the Evera™ and the Protecta™ ICD systems from Medtronic, the Ellipse™ ICD from St. Jude Medical and the INCEPTA™ ICD from Boston Scientific, have a battery which lasts on average 7 years, whereas known subcutaneous ICDs, such as the S-ICD™ from Cameron Health (now owned by Boston Scientific) require a battery replacement approximately every 5 years. In general, most IMDs are used to treat conditions which may accompany a patient for the duration of their life and as such, either the IMD or the power source must be replaced at some point in time. Whether the IMD is inserted via a fully invasive procedure or a minimally invasive procedure, when the batteries of the IMD are fully discharged, surgery is required to remove the IMD and replace it with a new one. As any kind of surgery involves potential health risks, there is a desire to increase the amount of time between battery replacements (and hence IMD replacements), thus reducing the number of surgeries a patient may go through while porting the IMD.

The design of state of the art IMDs has various constraints, one of them being size and weight. Whereas an increase in the size of the battery of an IMD may allow the IMD to function for a longer period of time, there is a constant motivation to reduce the physical size of IMDs such that they are less obtrusive to the patient and his body. One method for increasing the amount of time between battery replacements without increasing the size of the battery would be a more efficient battery which can store more charge per unit volume than current state of the art batteries. Another method is the use of rechargeable batteries which can be recharged wirelessly using energy transfer methods. Such batteries, also known as secondary cells, may not carry as much charge as a non-rechargeable battery, also known as a primary cell, however since they can be recharged, they may be able to power an IMD for a longer period of time before replacement is required. Even though secondary cells can only be recharged a finite number of times, the total amount of charge a rechargeable battery can give an IMD might be longer than the total charge stored on a primary cell, thereby increasing the time between battery replacements. For example, state of the art lithium-ion batteries can go through approximately 3000 charge-discharge cycles before requiring replacement, provided the batteries are completely discharged between cycles.

IMDs utilizing rechargeable batteries are known in the art. US Patent Application Publication No. 2008/0312725 A1, to Penner, assigned to E-Pacing, Inc., entitled "Implantable devices and methods for stimulation of cardiac and other tissues" is directed to an implantable system for stimulation of the heart, phrenic nerve or other tissue structures accessible via a patient's airway. The stimulation system includes an implantable controller housing which includes a pulse generator, an electrical lead attachable to the pulse generator and an electrode carried by the electrical lead. The electrode is positionable and fixable at a selected position within an airway of a patient. The controller housing may be adaptable for implantation subcutaneously, or alternatively, at a selected position within the patient's trachea or bronchus. The controller housing is proportioned to substantially permit airflow through the patient's airway around the housing. The pulse generator may be operable to deliver one or more electrical pulses effective in cardiac pacing, cardiac defibrillation, cardioversion, cardiac resynchronization therapy, or a combination thereof and includes a power source. In one embodiment, the system may further include a cannula adaptable for passage of the electrical lead through a wall of the trachea or bronchus. In another embodiment, the system may further include a tissue interface for wirelessly communicating an electrical signal through a wall of the trachea or bronchus. The power source may be a rechargeable power source, charged using electromagnetic charging. Other wireless charging methods may be used, for example, magnetic induction, radio frequency charging or light energy charging. The power source may also be charged by direct charging, such as via a catheter, through an endotracheal tube or during bronchoscopy, for example, to a charging receptacle, feedthrough or other interface optionally included in the pulse generator.

US Patent Application Publication No. 2010/0076524 A1, to Forsberg et al., assigned to Medtronic, Inc., entitled "Inductively rechargeable external energy source, charger, system and method for a transcutaneous inductive charger for an implantable medical device" is directed to a system that comprises an implantable medical device operationally coupled to receive energy from a secondary coil. An antenna is adapted to be positioned at a selected location relative to the secondary coil. An external power source is coupled to generate a signal in the antenna at any selected frequency that is within a predetermined frequency range to transcutaneously transfer energy from the antenna to the secondary coil when the implantable medical device is implanted in a patient. A core is selectably positionable relative to the antenna to focus the energy while the antenna is in the selected location.

This application is also directed to an improved mechanism for transcutaneously transferring energy from an external power source to an implantable medical device. The method comprises positioning an antenna in proximity of the implantable medical device, laterally adjusting a position of a core of the antenna relative to the implantable medical device while the antenna is maintained substantially stationary, and adjusting a frequency of transmission of a power source. The method may further comprise driving the antenna with the power source at the adjusted frequency to transfer energy transcutaneously to the implantable medical device.

US Patent Application Publication No. 2011/0004278 A1, to Aghassian et al., assigned to Boston Scientific Neuromodulation Corporation, entitled "External charger for a medical implantable device using field sensing coils to improve coupling" is directed to a method for assessing the alignment between an external charger and an implantable medical device. By incorporating magnetic field sensing coils in an external charger, it is possible to determine the position of an implantable device by sensing the reflected magnetic field from the implant. In one embodiment, two or more field sensing coils are arranged to sense the reflected magnetic field. By comparing the relative reflected magnetic field strengths of the sensing coils, the position of the implant relative to the external charger can be determined Audio and/or visual feedback can then be communicated to a patient to allow the patient to improve the alignment of the charger.

US Patent Application Publication No. 2012/0032522 A1, to Schatz et al., entitled "Wireless energy transfer for implantable devices" is directed to improved configurations for a wireless power transfer, employing repeater resonators to improve the power transfer characteristics between source and device resonators. A wireless energy transfer system for powering devices implanted in a patient is described. The system comprises a high-Q source resonator having a first resonant frequency, the source resonator being external to the patient, coupled to a power source and configured to generate oscillating magnetic fields at substantially a first resonant frequency. The system also comprises a high-Q device resonator having a second resonant frequency, the device resonator coupled to an implantable device requiring a supply power, the device resonator being internal to the patient and configured to capture the oscillating magnetic fields generated by the source resonator. The system further comprises a repeater resonator, wherein the repeater resonator is positioned to improve the energy transfer between the source resonator and the device resonator.

SUMMARY OF THE PRESENT DISCLOSED TECHNIQUE

It is an object of the disclosed technique to provide a novel method and system for recharging a flexible subcutaneous implantable medical device (IMD) having a rechargeable battery with a novel antenna configuration for enabling efficient recharging and significantly increasing the lifespan of the flexible subcutaneous IMD. It is also an object of the disclosed technique to provide a novel method for simultaneously recharging and communicating data wirelessly to a subcutaneous rechargeable IMD.

In accordance with the disclosed technique, there is thus provided a flexible subcutaneous IMD, including an elongated and flexible body, a plurality of electronic components, at least one rechargeable battery, at least one antenna, at least one lead and at least one transition unit. The rechargeable battery is for powering the plurality of electronic components, the antenna is for receiving and transmitting electromagnetic radiation, the lead is for providing an electric shock and the transition unit is for coupling the lead to at least one end of the elongated and flexible body. The elongated and flexible body is structured from a plurality of units. A first one of the plurality of units encapsulates the rechargeable battery and each one of the other plurality of units respectively encapsulates a respective one of the plurality of electronic components. The antenna is positioned in the transition unit and the transition unit is covered with a biocompatible polymer. The antenna receives electromagnetic radiation for recharging the rechargeable battery and includes a copper coil having a generally cylindrical shape.

In accordance with another embodiment of the disclosed technique, there is thus provided a wireless antenna configuration for a flexible subcutaneous IMD including a copper coil. The copper coil is wound around a hollow ferrite core, thereby giving the copper coil a generally cylindrical shape.

In accordance with a further embodiment of the disclosed technique, there is thus provided a method for simultaneously recharging and communicating data wirelessly to a subcutaneous rechargeable IMD. The method includes the procedures of transmitting electromagnetic radiation for recharging the subcutaneous rechargeable IMD and modulating the electromagnetic radiation for communicating data to the subcutaneous rechargeable IMD.

In accordance with another embodiment of the disclosed technique, there is thus provided a method for simultaneously recharging and communicating data wirelessly to a subcutaneous rechargeable IMD. The method includes the procedures of transmitting electromagnetic radiation over a channel for recharging the subcutaneous rechargeable IMD and simultaneously modulating the electromagnetic radiation over the channel for communicating data to the subcutaneous rechargeable IMD.

In accordance with a further embodiment of the disclosed technique, there is thus provided a subcutaneous IMD recharging system, including a flexible rechargeable subcutaneous IMD implanted in a patient and a charger transmitter. The flexible rechargeable subcutaneous IMD includes at least one receiver antenna and at least on rechargeable battery. The charger transmitter includes at least one transmitter antenna. The charger transmitter is for providing electromagnetic (EM) radiation to the receiver antenna wirelessly for recharging the rechargeable battery. The transmitter antenna is encased in a structure for temporarily coupling the transmitter antenna to the skin of the patient.

In accordance with another embodiment of the disclosed technique, there is thus provided a wireless antenna configuration for a flexible subcutaneous IMD including a flexible foil and an embedded copper antenna in the flexible foil. The flexible foil is folded over into a cylindrical shape.

In accordance with a further embodiment of the disclosed technique, there is thus provided a method for simultaneously recharging and communicating data wirelessly to a subcutaneous rechargeable IMD. The method includes the procedures of transmitting energy for recharging the subcutaneous rechargeable IMD and modulating the energy for communicating data to the subcutaneous rechargeable IMD.

In accordance with another embodiment of the disclosed technique, there is thus provided a flexible subcutaneous IMD including an elongated and flexible body, a plurality of electronic components, at least one rechargeable battery, at least one antenna and at least one lead. The rechargeable battery is for powering the plurality of electronic components, the antenna is for receiving and transmitting electromagnetic radiation and the lead is for providing an electric shock. The lead terminates at least one end of the elongated and flexible body. The elongated and flexible body is structured from a plurality of units. A first one of the plurality of units encapsulates the rechargeable battery and each one of the other plurality of units respectively encapsulates a respective one of the plurality of electronic components. At least one of the plurality of units may be electrically active. The antenna is positioned around at least one of the plurality of units which is not electrically active. The antenna is covered with a biocompatible polymer and receives electromagnetic radiation for recharging the rechargeable battery.

BRIEF DESCRIPTION OF THE DRAWINGS

The disclosed technique will be understood and appreciated more fully from the following detailed description taken in conjunction with the drawings in which:

FIG. 1 is a schematic illustration of a flexible subcutaneous IMD with a rechargeable battery, constructed and operative in accordance with an embodiment of the disclosed technique;

FIG. 2A is a schematic illustration of a first receiver antenna, shown in various views, constructed and operative in accordance with another embodiment of the disclosed technique;

FIG. 2B is a schematic illustration of a second receiver antenna, shown in various views, constructed and operative in accordance with a further embodiment of the disclosed technique;

FIG. 5 is a schematic illustration of a flexible subcutaneous IMD with a rechargeable battery showing possible placements of a receiver antenna within the IMD, constructed and operative in accordance with another embodiment of the disclosed technique;

FIG. 6 is a schematic illustration showing the coupling between a receiver antenna and a rechargeable battery in a flexible subcutaneous IMD, constructed and operative in accordance with a further embodiment of the disclosed technique;

FIG. 7 is a schematic illustration of a transmitter for transferring energy to a receiver antenna, constructed and operative in accordance with another embodiment of the disclosed technique;

DETAILED DESCRIPTION OF THE EMBODIMENTS

Figure 3A:
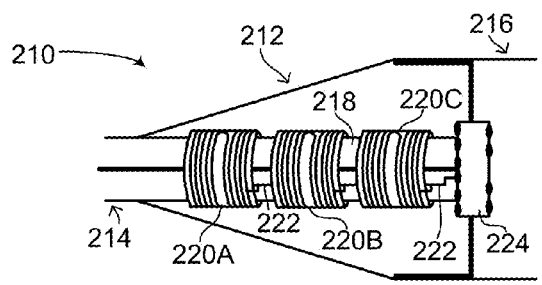
FIG. 3A is a schematic illustration of the first receiver antenna of FIG. 2A positioned in a transition unit of the flexible subcutaneous IMD of FIG. 1, constructed and operative in accordance with another embodiment of the disclosed technique.

The disclosed technique overcomes the disadvantages of the prior art by providing a novel flexible subcutaneous IMD having a rechargeable battery with a novel antenna configuration for enabling efficient recharging of the rechargeable battery and significantly increasing the lifespan of the flexible subcutaneous IMD. The disclosed technique also includes a novel method for budgeting energy in the flexible subcutaneous IMD thereby further increasing its lifespan.

Reference is now made to FIG. 1, which is a schematic illustration of a flexible subcutaneous IMD with a rechargeable battery, generally referenced 100, constructed and operative in accordance with an embodiment of the disclosed technique. Flexible subcutaneous IMD 100 (herein referred to also as merely IMD 100) is shown as a flexible subcutaneous ICD 100 for the purposes of illustrating the disclosed technique, however the disclosed technique applies to any flexible IMD that can be placed in a patient subcutaneously and has the following general features:

1. An elongated and flexible body, with at least one end of the IMD terminating with a lead;

2. Wherein the elongated and flexible body is structured from a plurality of units or links, each unit or link containing an electronic component of the IMD; and 3. Wherein at least one of the units or links may be active.

According to the disclosed technique, IMD 100 can thus be a flexible subcutaneous ICD, a pacemaker, a neurostimulation device, a combined pacing and ICD device, a monitoring device and the like and can be used for treating various types of medical conditions, such as various kinds of arrhythmias, like ventricular fibrillation and tachycardia, as well as chronic pain. It is noted as well that even though the disclosed technique is described throughout as applying to subcutaneously placed IMDs, the disclosed technique is not limited to IMDs only placed subcutaneously. The disclosed technique relates to IMDs placed in other parts of the body of a patient provided sufficient charging efficiency is achievable. This is usually a function of the distance between the placement of the IMD and the outer surface of the skin of the patient. Any kind of IMD placement in the body of a patient in which the distance between the IMD and the outer surface of the skin of the patient is within approximately 10 millimeters is considered applicable to the disclosed technique.

Flexible subcutaneous ICD 100 includes an elongated and flexible body 102, a plurality of leads 106A and 106B and a respective plurality of transition units 104A and 104B. Plurality of transition units 104A and 104B respectively couple plurality of leads 106A and 106B with elongated and flexible body 102. Each one of plurality of leads 106A and 106B includes a lead end 112. Lead end 112 includes a non-active section 114, a shocking coil 116, a first sensor 118, a second sensor 120, a rounded tip 122 and a suture eyelet 124. First sensor 118 and second sensor 120 flank either side of shocking coil 116. First sensor 118 and second sensor 120 can be used for sensing various physiological parameters of a heart (not shown), such as the temperature of the surrounding tissue (not shown), electrical activity in the surrounding tissue and the like. In the general case of IMD 100, first sensor 118 and second sensor 120 may be used for sensing various physiological parameters of an organ of interest (not shown), such as the brain, the lungs, the stomach, the intestines and the like. In general, lead end 112 is made from a flexible material and can be optionally covered with a biocompatible material. It is noted that IMD 100 may include at least one sensor and not necessarily two sensors (or more) as shown in FIG. 1.

Elongated and flexible body 102 includes a plurality of links 108 which encapsulates all the electronics of flexible subcutaneous ICD 100, such as at least one rechargeable battery (not shown), at least one capacitor (not shown), at least one processor (not shown) and at least one high voltage unit (not shown) for charging the capacitor. The rechargeable battery is for powering the processor and storing charge on the capacitor. The processor is for receiving signals from first sensor 118 and second sensor 120 and for determining when an electrical shock via shocking coil 116 should be applied to the heart. The processor also determines others parameters of the electrical shock, such as the voltage, the time duration, the phase, the number of shocks and the like. The high voltage unit is for converting the low voltage of the rechargeable battery to the high voltage required for the electrical shock and for storing the high voltage on the capacitor. As shown, plurality of links 108 includes a plurality of outer units 126A, 126B, 126C and 126N, which are each coupled with one another via one of a bellows, an accordion-like shape structure, a ball-and-socket structure (all not shown) and the like, for providing a degree of flexibility between each one of plurality of outer units 126A-126N. Each one of plurality of outer units 126A-126N encapsulates an electronic component of flexible subcutaneous ICD 100, such as plurality of electronic components 128A, 128B, 128C and 128N. Each one of plurality of electronic components 128A-128N could be one of a rechargeable battery, a capacitor, a high voltage unit or a processor, as described above. Elongated and flexible body 102 in general has either a cylindrical, circular or elliptical cross-section, although elongated and flexible body 102 may also be embodied as a flat structure, having a rectangular or polygonal cross-section.

In general, plurality of links 108 is not active and does not function as an electrode, although in some embodiments of the disclosed technique at least one of the links may be active and can function as an electrode. Even though elements of plurality of links 108, such as plurality of outer units 126A-126N, may be made from metal, each one of plurality of links 108 in general is covered with a biocompatible polymer and electric current is not run or conducted through any of plurality of outer units 126A-126N. This is unlike state of the art ICDs or other types of IMDs which include a can and leads design, such as the Evera™ and the Protecta™ ICD systems mentioned above, as well as the Ellipse™ ICD and the INCEPTA™ ICD also mentioned above. In these ICDs and IMDs, the can houses all the electronic components and also acts as an active electrode. As mentioned above, most of the links in plurality of links 108 are not active, although plurality of links 108 can be designed such that particular outer units individually act as active electrodes. For example, outer unit 126C is shown filled in with hatched lines, thus representing an active outer unit. However the other outer units shown in FIG. 1 are not active.

Plurality of transition units 104A and 104B each include a respective strain relief 110A and 110B. Strain reliefs 110A and 110B each include a tapered shape, thus transitioning the larger outer diameter (not shown) of plurality of links 108 to the smaller outer diameter (not shown) of lead end 112. Strain reliefs 110A and 110B are shown in greater detail below in FIGS. 3A and 3B. Strain reliefs 110A and 110B enable any wiring in lead end 112 to be coupled with plurality of links 108, while maintaining a hermetic seal (not shown) on elongated and flexible body 102, thereby preventing any liquids and/or bodily fluids from entering elongated and flexible body 102.

Flexible subcutaneous ICD 100 includes at least one rechargeable battery (not shown specifically). For example, electronic components 128A and 128B may be rechargeable batteries. The rechargeable batteries may be lithium-ion, nickel-cadmium, nickel-metal hydride, lithium polymer or silver-zinc batteries. State of the art ICDs having a can and leads designs, such as the Evera™ ICD, the Protecta™ ICD, the Ellipse™ ICD and the INCEPTA™ ICD, all mentioned above, each includes a non-rechargeable battery which must be replaced substantially every 7 years. Since the battery is not rechargeable, the entire ICD must be replaced, or at minimum, the can which houses the non-rechargeable battery. These ICDs are not subcutaneous, therefore more involved surgery may be necessary for removing and replacing the can of the ICD. On the market subcutaneous ICDs, such as the S-ICD™ mentioned above, need to be replaced substantially every 5 years. Whereas such subcutaneous ICDs have a shorter life span due to a larger battery storing more energy but for a shorter amount of time, as compared to an intracardiac ICD, since they are placed subcutaneously, their removal and replacement are simpler and involve less invasive surgery than a standard state of the art ICD as described above, mainly because such ICDs do not include transvenous leads. According to the disclosed technique, flexible subcutaneous ICD 100 includes at least one rechargeable battery, which is charged periodically over its lifespan. Due to the rechargeable nature of the power source of flexible subcutaneous ICD 100, the rechargeable batteries of flexible subcutaneous ICD 100 or the IMD itself, need only be replaced substantially every 10 years. Since flexible subcutaneous ICD 100 is placed subcutaneously in a patient, flexible subcutaneous ICD 100 has the advantage, like other subcutaneous IMDs, of requiring only minimally invasive surgery for removing and replacing the IMD and/or rechargeable batteries. Flexible subcutaneous ICD 100 also provides a substantially extended lifespan over prior art IMDs due to a concept shift in how rechargeable subcutaneous IMDs store and use energy to function. Prior art IMDs, such as prior art ICDs, whether intracardiac or subcutaneous, are designed to store enough energy to last the lifetime of the device. In the case of intracardiac ICDs this is about 7 years and in the case of subcutaneous ICDs this is about 5 years. In the disclosed technique, less energy is stored in a smaller sized battery that can be recharged multiple times. There is thus no need in the disclosed technique to store enough charge on the battery for the entire lifetime of the device which enables the device to function longer within the body of a patient.

Flexible subcutaneous ICD 100 includes an energy budget for enabling the IMD to actively function for substantially two years before requiring a recharge. This includes sufficient energy for operating at least one processor for receiving various signals from first sensor 118 and second sensor 120 and for determining if, when and how electrical shocks are to be delivered to a patient in case an arrhythmia is detected via at least one of first sensor 118 and second sensor 120. Of the various possible arrhythmias flexible subcutaneous ICD 100 can handle and treat, ventricular fibrillation (herein abbreviated VF), which can lead to sudden cardiac arrest (herein abbreviated SCA), requires the most amount of energy to treat. The energy budget of flexible subcutaneous ICD 100 thus also includes sufficient energy to store up to ten high voltage electrical shocks for treating VF and possibly SCA. For example, a typical energy budget according to the disclosed technique might divide the total energy available from the rechargeable batteries over the course of approximately 2 years such that about ⅔ of the available energy is available for administering electrical shocks in case VF is detected and if SCA then ensues, up to a maximum of two such episodes before recharging is required, whereas about ⅓ of the available energy is used for the continuous operation of the IMD, such as monitoring electrical activity of the heart.

Thus, flexible subcutaneous ICD 100 stores enough charge in its rechargeable batteries to provide ten high voltage electrical shocks and to operate continuously for about two years. According to the disclosed technique, once a predefined percentage of the charge stored in flexible subcutaneous ICD 100 has been used up, such as 50%, 60%, 75% and the like, then flexible subcutaneous ICD 100 should be recharged to maximum capacity. In general, common practice in the field of implantable ICDs is for a patient to visit his or her physician, such as an electrophysiologist or cardiologist, once every three months for a general check-up and to verify the working of the ICD. It is thus reasonable that a patient with flexible subcutaneous ICD 100 implanted inside him would be required to visit his physician at least once a year, or possibly more frequently, for a general check-up and to verify the working of the flexible subcutaneous ICD. Such a requirement is well within the energy budget of flexible subcutaneous ICD 100, which is designed to function for about two years given the charge stored therein. Under proper use then, the patient will be visiting his or her physician while the IMD still has enough charge to function. At each, or some of these visits, the physician may verify the current charge level of the rechargeable batteries and decide if the rechargeable batteries should be recharged at the visit or at a subsequent visit. In addition, the IMD may communicate with a monitoring device, such as a smartphone of the patient, on a daily basis, reporting the charge status of the rechargeable battery of the IMD. The charge status can be then presented on the monitoring device to the user or patient, in addition to providing an alarm or warning signal in case of insufficient charge remaining in the rechargeable battery.

The energy budget of flexible subcutaneous ICD 100 is designed to allow for up to five high voltage electrical shocks to be provided to a patient if an episode of VF or SCA is detected. After each single high voltage electrical shock, first sensor 118 and second sensor 120 are used to detect electrical signals from the heart of the patient. The electrical signals are then provided to the processor of flexible subcutaneous ICD 100 which uses an algorithm and processing to determine if the VF episode has been treated or if an additional high voltage electrical shock is required, or if the heart of the patient (not shown) has restarted after SCA. The algorithm and processing might take into account various possible sensing vectors between first sensor 118 and second sensor 120, as well acoustic data in the chest cavity of the patient from a microphone (not shown) embedded in flexible subcutaneous ICD 100. A weighted algorithm might be used to combine electrical data garnered from first sensor 118 and second sensor 120 and heartbeat data garnered from the microphone. This continues up to five high voltage electrical shocks. The energy budget of flexible subcutaneous ICD 100 is thus designed to handle and treat two continuous episodes of VF or SCA. It is considered reasonable that after a patient suffers an episode of VF or SCA, he or she will immediately go either to the hospital or a clinic to have a check-up with their physician. As described further below, flexible subcutaneous ICD 100 includes a wireless transmitter and receiver (not shown in FIG. 1) and can communicate messages to the patient, the physician, a call center and the like. Therefore, the patient may be quickly alerted, for example via a message to his smartphone, that flexible subcutaneous ICD 100 detected an episode of VF or SCA and treated it with three high voltage electrical shocks and that the patient should immediately contact his physician and go in for a check-up. As flexible subcutaneous ICD 100 stores enough charge for up to two episodes of VF or SCA, the visit at the physician after such an episode should be used to recharge the rechargeable batteries such that there is enough charge again to handle and treat two episodes of VF or SCA. The energy budget of flexible subcutaneous ICD 100 includes enough charge to handle two episodes of VF or SCA in order to cover the case of a patient who suffers an episode of VF or SCA, which is treated by the subcutaneous ICD, and when on his way to the physician, experiences another episode of VF or SCA. Flexible subcutaneous ICD 100 thus includes a 'spare' set of high voltage electrical treatment shocks in the event that a patient experiences two episodes of VF or SCA before making it to his or her physician's clinic or office for a check-up, additional treatment and/or a recharge of their subcutaneous ICD. As mentioned above, the rechargeable batteries of flexible subcutaneous ICD 100 can store sufficient charge to charge the at least one capacitor in flexible subcutaneous ICD 100 with sufficient charge to deliver up to ten high voltage electrical shocks to a patient within a period of approximately two years. It is noted that the mention of a charge period of about two years in simply brought as an example and that flexible subcutaneous ICD 100 may store sufficient charge for other periods of time, such as 1 year, 3 years and the like.

As described below in greater detail in FIGS. 3A, 3B, 4A and 4B, flexible subcutaneous ICD 100 includes a wireless power receiver (not shown in FIG. 1). The wireless power receiver can receive energy wirelessly and convert it to a form of energy for charging the rechargeable batteries of flexible subcutaneous ICD 100. According to the disclosed technique, a wireless power transmitter (not shown in FIG. 1) is also provided which transmits power to the wireless power receiver. The wireless power transmitter is shown and explained in greater detail below in FIGS. 7, 8 and 9. In general, the wireless power transmitter will be located at a physician's clinic or at a hospital, which is where a patient will have to go to recharge the rechargeable batteries of their flexible subcutaneous ICD. In another embodiment of the disclosed technique, the wireless power transmitter can be located with the patient. The wireless power receiver is located internally within flexible subcutaneous ICD 100 whereas the wireless power transmitter is located externally to flexible subcutaneous ICD 100 and is a standalone device. Due to the subcutaneous placement of flexible subcutaneous ICD 100, the wireless power transmitter can be positioned proximate to the wireless power receiver in the IMD. The short distance between the wireless power transmitter and the wireless power receiver, for example, around 1 centimeter (herein abbreviated cm) or less, enables a quick and efficient charge of the rechargeable batteries of flexible subcutaneous ICD 100. In general, charge efficiency decreases with distance, therefore it is advantageous to keep the distance between the wireless power receiver and wireless power transmitter to a minimum in order to increase charge efficiency as much as possible. According to the disclosed technique, for example, at a distance of approximately 8-10 millimeters between the wireless power receiver and wireless power transmitter, the wireless power receiver can receive enough charge to recharge the rechargeable batteries of the IMD from about 50% charge to fully charged (i.e., 100% charged) in approximately an hour.

Most prior art rechargeable IMDs are designed for low energy applications that do not require high voltage electrical shocks as treatment, such as pacemakers and stimulators. In addition, prior art ICDs having a can and leads design in which the leads are not placed subcutaneously nevertheless require high voltage electrical shocks for the treatment of cardiac fibrillation when the leads are placed intracardially. In flexible subcutaneous ICD 100, the voltage required for providing a treatment is even higher since lead ends 112 are not placed intracardially. The novel configuration of the wireless power receiver in flexible subcutaneous ICD 100, as described below in FIGS. 2A-4B, enables flexible subcutaneous ICD 100 to be recharged within a short amount of time (such as about 1-2 hours) approximately once every year wherein a significantly high amount of charge is required to meet the energy budget of flexible subcutaneous ICD 100. Current prior art rechargeable IMDs in general require more frequent charging periods, for example between once a day to once a month, depending on the active program selected in such prior art rechargeable IMDs. The flexible subcutaneous IMD of the disclosed technique also provides a novel design wherein a receiver antenna can be effectively placed to receive energy wirelessly to charge a rechargeable battery of the IMD sufficiently for 1-2 years' worth of operation.

An inherent issue in wireless energy transfer relates to the radiation profile of the energy transmitted from a power transmitter and the topological configuration of the power receiver to receive the energy transmitted. In general, power transmitters tend to have a wide radiation profile or wide antenna footprint, for maximizing the amount of energy they can transfer per unit of time. Yet as can be seen in FIG. 1, flexible subcutaneous ICD 100 has a long yet thin and narrow shape, affording flexible subcutaneous ICD 100 minimal surface area, i.e., a narrow profile or narrow antenna footprint, for receiving the energy transmitted. As described below in FIG. 8, since flexible subcutaneous ICD 100 has a round cross-section, the perpendicular surface of the IMD for receiving energy from a power transmitter is substantially narrow. According to the disclosed technique, as described below in FIGS. 2A and 2B, novel antenna configurations are disclosed which enable an IMD having a long yet thin shape to maximize the amount of energy received such that efficient energy transfer can occur between a power transmitter having a wide antenna footprint and a power receiver on an IMD, where the IMD topologically has a narrow antenna footprint.

Reference is now made to FIG. 2A, which is a schematic illustration of a first receiver antenna, shown in various views, generally referenced 150, constructed and operative in accordance with another embodiment of the disclosed technique. First receive antenna 150 is shown in various orthogonal projections as indicated by an arrow 152A and in various perspective projections as indicated by an arrow 152B. First receiver antenna 150 represents a first possible novel antenna configuration for enabling a high energy level transfer between the wireless power transmitter and the wireless power receiver with a high charging efficiency which is relatively rapid. As described below, first receiver antenna 150 enables a high level of energy, such as approximately 10 watts, to be transferred from a wireless power transmitter to a wireless power receive located inside an IMD of the disclosed technique in approximately under 2 hours. The wireless power transmitter might include a plurality of transmitter antennas, for example two antennas, where each antenna transfers approximately 5 watts of energy during a recharge procedure.

As shown in orthogonal projections 152A, first receiver antenna 150 has a generally rectangular shape and includes a flexible foil 154 and a copper antenna 156. First receiver antenna 150 is substantially two dimensional (herein also referred to as 2D). Copper antenna 156 is overlaid on flexible foil 154, in a manner similar to how printed circuits are manufactured. Flexible foil 154 can be made from any biocompatible metal material, such as titanium. Such a biocompatible metal material can be vaporized as the antenna substrate. Depending on the material used, in the case of the antenna substrate not being flexible, cracks can be prevented in the substrate by preforming it to be cylindrical and thus positioned around an outer unit of a subcutaneous flexible IMD, as described below in FIGS. 4A and 4B. Copper antenna 156 can be overlaid on flexible foil 154 in any known shape or pattern for maximizing the amount of covered surfaced area over flexible foil 154. According to the disclosed technique, first receiver antenna 150 is folded over into a cylindrical shape, thereby giving it a three dimensional (herein also referred to as 3D) shape as shown in perspective projections 152B. This is shown schematically as arrows 158A and 158B, which indicate the direction in which flexible foil 154 is folded in to create the shapes shown in perspective projections 152B. As shown in a frontal orthogonal projection, flexible foil 154 has a rectangular shape, whereas in the perspective projection, once folded, flexible foil 154 has a cylindrical shape. A line 160 shows where opposite ends (not labeled) of flexible foil 154 meet once folded into a cylindrical shape. The opposite ends may be coupled together such that flexible foil 154 retains its cylindrical shape. As shown in a side orthogonal projection, flexible foil 154 has a thin, almost line-like cross-section, whereas in the perspective projection, once folded, flexible foil 154 has a circular cross-section.

Reference is now made to FIG. 2B, which is a schematic illustration of a second receiver antenna, shown in various views, generally referenced 180, constructed and operative in accordance with a further embodiment of the disclosed technique. Second receiver antenna 180 is shown in a perspective projection as indicated by an arrow 182A and in an orthogonal projection as indicated by an arrow 182B. Second receiver antenna 180 represents a second possible novel antenna configuration for enabling a high energy level transfer between the wireless power transmitter and the wireless power receiver with a high charging efficiency which is relatively rapid. Second receiver antenna 180 is made from a copper coil 184. As shown, copper coil 184 is wound around a hollow ferrite core (not shown), thereby giving copper coil 184 its coil shape as shown in perspective projection 182A. The hollow ferrite core also increases the amount of received energy which can be concentrated onto copper coil 184. As shown in orthogonal projection 182B, second receiver antenna 180 has a circular cross-section. Like first receiver antenna 150 (FIG. 2A), second receiver antenna 180 has a generally cylindrical shape.

Both first receiver antenna 150 and second receiver antenna 180 maximize the surface area over which transmitted energy can be received. First receiver antenna 150 and second receiver antenna 180 both represent general configurations for an antenna to be used as part of the disclosed technique. As described below in FIGS. 3A-4B, an actual power receiver antenna may include a plurality of antennas having either one of the configurations as shown in FIGS. 2A and 2B. Each individual antenna (in either configuration) includes two ends (not labeled) via which additional antennas can be coupled to it in series. The ends of the power receiver antenna can then be coupled with a bus (not shown) and/or with electronics (not shown) in an IMD (not shown) for transferring the received energy to a rechargeable battery (not shown). It is noted that in the case of a plurality of antennas being coupled together to form the power receiver antenna of the disclosed technique, a semi-circular shaped, 'C'-shaped or 'U'-shaped coupler may be used to couple between individual antennas for added flexibility between individual antennas.

The flexible nature of first receiver antenna 150 (FIG. 2A) and second receiver antenna 180 enables them to conform to the shape of a flexible subcutaneous IMD, such as flexible subcutaneous ICD 100 (FIG. 1). In addition, their generally cylindrical shape makes them omnidirectional for receiving transmitted energy from any direction with no limitation or preference to the roll orientation of the antenna, thus once they are placed inside an IMD, the IMD does not require a specific orientation once placed inside a patient to maximize the amount of received energy. This is shown in greater detail in FIGS. 3A-4B below. It is also noted that first receiver antenna 150 and second receiver antenna 180 may be made from a biocompatible material, which allows for long term use and functioning (i.e., years) while inside the flexible subcutaneous IMD without causing harm or damage to body tissue surrounding the IMD and without being compromised mechanically and electrically due to bodily fluids, gases and the like, which the IMD can come in contact with while implanted in a patient.

Reference is now made to FIG. 3A, which is a schematic illustration of the first receiver antenna of FIG. 2A positioned in a transition unit of the flexible subcutaneous IMD of FIG. 1, generally referenced 210, constructed and operative in accordance with another embodiment of the disclosed technique. As shown, a transition unit 212 of a flexible subcutaneous IMD couples a lead 214 with an elongated flexible body 216. Lead 214 is coupled with a dielectric feed-through 224 which enables electrical connections between elongated flexible body 216 with transition unit 212 and lead 214 while not compromising a hermetic seal on elongated flexible body 216. Lead 214 has a lead body 218, which may be cylindrical in shape. In the embodiment shown in FIG. 3A, a wireless power receiver is shown having a plurality of antennas 220A, 220B and 220C. Each one of plurality of antennas 220A-220C has a configuration like first receiver antenna 150 (FIG. 2A). As shown, each one of plurality of antennas 220A-220C is coupled with a bus 222 which is coupled with dielectric feed-through 224, thereby enabling any energy received by plurality of antennas 220A-220C to be transferred electrically into elongated flexible body 216. Alternatively, plurality of antennas 220A-220C may be coupled in series (not shown), thereby having only a single connection to bus 222. In addition, plurality of antennas 220A-220C may be embodied as a single antenna (not shown). As shown in FIG. 3A, each one of plurality of antennas 220A-220C is wrapped around lead body 218. Plurality of antennas 220A-220C may be coupled to bus 222 via a Y-shaped cable (not shown). In this manner, only one coupling point is required between plurality of antennas 220A-220C and dielectric feed-through 224 which couples with electronics (not shown) and rechargeable batteries (not shown) located within elongated flexible body 216. A single coupling point for plurality of antennas 220A-220C thus minimizes the exposure of the components, located within elongated flexible body 216, to moisture and bodily fluids.

Figure 3B:
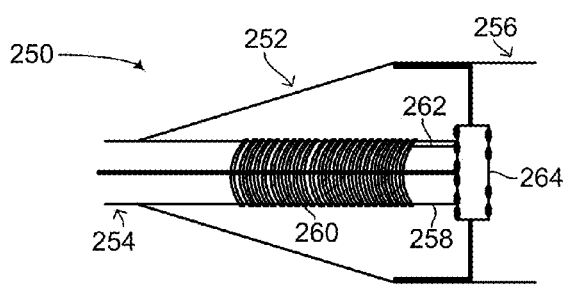
FIG. 3B is a schematic illustration of the second receiver antenna of FIG. 2B positioned in a transition unit of the flexible subcutaneous IMD of FIG. 1, constructed and operative in accordance with a further embodiment of the disclosed technique.

Reference is now made to FIG. 3B, which is a schematic illustration of the second receiver antenna of FIG. 2B positioned in a transition unit of the flexible subcutaneous IMD of FIG. 1, generally referenced 250, constructed and operative in accordance with a further embodiment of the disclosed technique. As shown, a transition unit 252 of a flexible subcutaneous IMD couples a lead 254 with an elongated flexible body 256. Lead 254 is coupled with a dielectric feed-through 264 which enables electrical connections between elongated flexible body 256 with transition unit 252 and lead 254 while not compromising a hermetic seal on elongated flexible body 256. Lead 254 has a lead body 258, which may be cylindrical in shape. In the embodiment shown in FIG. 3B, a wireless power receiver is shown having a single antenna 260, having a configuration like second receiver antenna 180 (FIG. 2B). As shown, antenna 260 is coupled with a bus 262 which is coupled with dielectric feed-through 264, thereby enabling any energy received by antenna 260 to be transferred electrically into elongated flexible body 256. In addition, antenna 260 may be embodied as a plurality of antennas (not shown), each having a configuration like second receiver antenna 180. As shown in FIG. 3B, due to the coil shape of antenna 260, it can be wrapped around lead body 258.

The cylindrical nature of the antennas shown in FIGS. 3A and 3B increase their respective antenna footprint while also making them omnidirectional and thus able to receive energy from substantially any perpendicular direction to the outer surface of the transition unit. As shown, the antennas are placed within a component of a flexible subcutaneous IMD (for example, a transition unit) and are not placed on the outer surface of the IMD, thus protecting the antennas from bodily fluids. As described below in FIG. 5, a flexible subcutaneous IMD of the disclosed technique with rechargeable batteries may include a single antenna for receiving energy to recharge the batteries, two antennas (thus forming a dual-antenna system) or a plurality of antennas (thus forming a multi-antennae system).

Figure 4A:
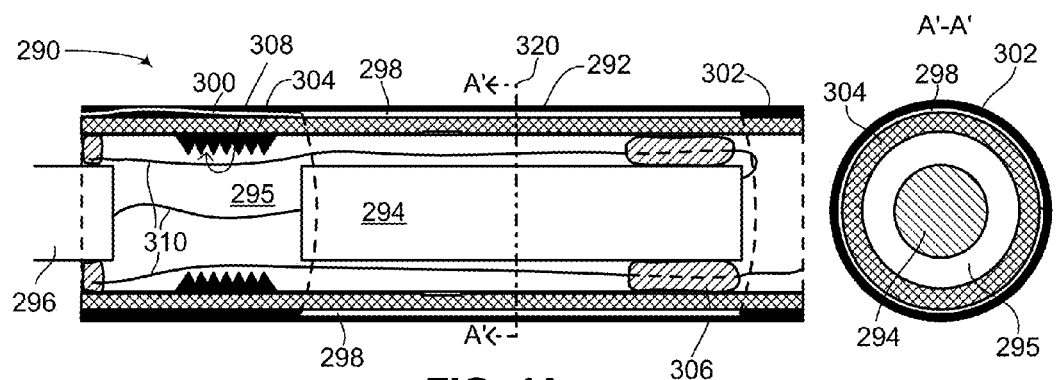
FIG. 4A is a schematic illustration of the first receiver antenna of FIG. 2A positioned in an outer unit of the flexible subcutaneous IMD of FIG. 1, constructed and operative in accordance with another embodiment of the disclosed technique.

Reference is now made to FIG. 4A, which is a schematic illustration of the first receiver antenna of FIG. 2A positioned in an outer unit of the flexible subcutaneous IMD of FIG. 1, generally referenced 290, constructed and operative in accordance with another embodiment of the disclosed technique. An outer unit 292 is shown which forms part of an elongated flexible body (not shown) of a flexible subcutaneous IMD (not shown). Outer unit 292 is hermetically sealed and includes an inner component 294. Inner component 294 may be a battery, a capacitor or electronics. Shown as well partially is an additional inner component 296, electrically coupled with inner component 294. The inner components (not all shown) in the elongated flexible body are coupled via a plurality of wires 310 and are also coupled with a dielectric feed-through (not shown). Inner component 294 has a bellows or accordion-shaped section 308, giving it a degree of flexibility. Inside outer unit 292, a biocompatible glue or epoxy 306 may be used to hold inner component 294 in place. Epoxy 306 is located in a space 295 which may be filled with a gas (not shown). The outer surface of outer unit 292 may be covered with a thin layer of metal 304 to hermetically seal the elongated flexible body. Thin layer of metal 304 may be covered with a polymer 302, such as Parylene, for giving the outer surface of outer unit 292 a smooth finish, making the elongated flexible body easier to position subcutaneously in a patient.

As shown in FIG. 4A, an antenna 298 is positioned around outer unit 292 between thin layer of metal 304 and polymer 302. Dotted lines (not labeled) show the outline of antenna 298 through space 295. Outer unit 292 may have a circular cross-section. Antenna 298 has the configuration of first receiver antenna 150 (FIG. 2A). Due to the flexibility of the flexible foil (not labeled) of antenna 298, antenna 298 can easily be wrapped around the outer surface of thin layer of metal 304, thus maximizing its antenna footprint, as shown. Antenna 298 can be coupled with other components in the elongated flexible body via a bus 300 which runs along the length of outer unit 292 between thin layer of metal 304 and polymer 302. Bus 300 may couple with a dielectric feed-through (not shown) located along outer unit 292 or in a transition unit (not shown) coupled with outer unit 292. In this embodiment, antenna 298 is shown as only including a single receiver antenna. However, antenna 298 may be embodied as a plurality of receiver antennas (not shown) which are coupled in series, wherein the receiver antennas are wrapped around a single outer unit or multiple outer units, as shown above in FIG. 3A. A cross-sectional view of the placement of antenna 298 around outer unit 292 is shown via an arrow 320, demarcating a cross-sectional view A'-A'. The cross-sectional view A'-A' shows antenna 298 wrapped around outer unit 292, sandwiched between thin layer of metal 304 and polymer 302. In general, outer unit 292 is made from metal. By wrapping antenna 298 around outer unit 292, specifically around thin layer of metal 304, antenna 298 is also substantially close to outer unit 292. When electromagnetic radiation is transmitted to antenna 298, outer unit 292 thereby acts as an energy concentrator, concentrating electromagnetic radiation to itself. Antenna 298, which is in close proximity to outer unit 292 from the outside, can thus achieve a high efficiency of energy reception due to the energy concentration of outer unit 292.

Figure 4B:
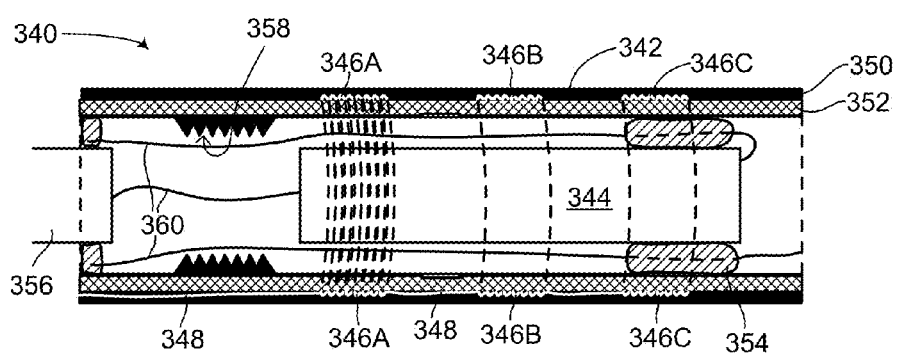
FIG. 4B is a schematic illustration of the second receiver antenna of FIG. 2B positioned in an outer unit of the flexible subcutaneous IMD of FIG. 1, constructed and operative in accordance with a further embodiment of the disclosed technique.

Reference is now made to FIG. 4B, which is a schematic illustration of the second receiver antenna of FIG. 2B positioned in an outer unit of the flexible subcutaneous IMD of FIG. 1, generally referenced 340, constructed and operative in accordance with a further embodiment of the disclosed technique. An outer unit 342 is shown which forms part of an elongated flexible body (not shown) of a flexible subcutaneous IMD (not shown). Outer unit 342 is hermetically sealed and includes an inner component 344. Inner component 344 may be a battery, a capacitor or electronics. Shown as well partially is an additional inner component 356, electrically coupled with inner component 344. The inner components (not all shown) in the elongated flexible body are coupled via a plurality of wires 360 and are also coupled with a dielectric feed-through (not shown). Inner component 344 has a bellows or accordion-shaped section 358, giving it a degree of flexibility. Inside outer unit 342, a biocompatible glue or epoxy 354 may be used to hold inner component 344 in place. The outer surface of outer unit 342 may be covered with a thin layer of metal 352 to hermetically seal the elongated body. Thin layer of metal 352 may be covered with a polymer 350, such as Parylene, for giving the outer surface of outer unit 342 a smooth finish, making the elongated flexible body easier to position subcutaneously in a patient.

As shown in FIG. 4B, a plurality of antennas 346A, 346B and 346C are positioned around outer unit 342 between thin layer of metal 352 and polymer 350. Dotted lines (not labeled) show the outline of plurality of antennas 346A, 346B and 346C. For illustrative purposes, antenna 346A is additionally shown with a plurality of dotted lines outlining all the turns of antenna 346A around outer unit 342. In order to not crowd FIG. 4B, that plurality of dotted lines is not shown for antennas 346B and 346C, however they are present. Each of plurality of antennas 346A-346C may be coupled with a bus 348 for coupling the antennas with other components in the elongated flexible body. Bus 348 runs along the length of outer unit 342 between thin layer of metal 352 and polymer 350. Bus 348 may couple with a dielectric feed-through (not shown) located along outer unit 342 or in a transition unit (not shown) coupled with outer unit 342. Outer unit 342 may have a circular cross-section. Plurality of antennas 346A-346C have the configuration of second receiver antenna 180 (FIG. 2B). Due to their coil shape, plurality of antennas 346A-346C can easily be wound and coiled around the outer surface of outer unit 342, thus maximizing its antenna footprint, as shown. Plurality of antennas 346A-346C may also be embodied as a single coil shaped antenna, as shown above in FIG. 3B. As can be seen in FIGS. 3A-4B, according to the disclosed technique a wireless power receiver antenna is formed for receiving energy by either a flexible foil with overlaid copper, where the copper windings are aligned with the outer surface of the elongated flexible body section of the IMD or via a coil where the direction of the windings is orthogonal to the outer surface of the elongated flexible body section of the IMD. Prior art IMDs which include an active can or active housing have a transmission-reception issue when it comes to wireless transmission. The can or housing is usually made of metal and is hermetically sealed, thus effectively forming a Faraday cage. Therefore placing a wireless power receiver antenna in such a can or housing would not enable wireless transmission due to the Faraday cage formed by the can or housing. In addition, since such cans and housings are active and serve as active electrodes, a wireless power receiver antenna also cannot be placed on their outer surface, as the active nature of such surfaces would interfere with wireless transmissions to and from such receiver antennas. This is unlike the disclosed technique in which the wireless power receiver antenna is placed over a non-active unit, therefore avoiding the interference issue, yet also placed outside a hermetically sealed metal unit, thus avoiding the Faraday cage issue as well.

Reference is now made to FIG. 5, which is a schematic illustration of a flexible subcutaneous IMD with a rechargeable battery showing possible placements of a receiver antenna within the IMD, generally referenced 390, constructed and operative in accordance with another embodiment of the disclosed technique. Flexible subcutaneous IMD 390 is substantially similar to flexible subcutaneous IMD 100 (FIG. 1) and is shown embodied as a flexible subcutaneous ICD 390. Flexible subcutaneous ICD 390 includes an elongated flexible plurality of units 392, a plurality of leads 396A and 396B and a respective plurality of transition units 394A and 394B. Plurality of transition units 394A and 394B respectively couple plurality of leads 396A and 396B with elongated flexible plurality of units 392. According to the disclosed technique, as explained in further detail below, since energy is to be transferred wirelessly between a transmitter (not shown) and at least one receiver (not shown) at maximum efficiency, the distance between the transmitter and the receiver antennas (not shown) should be minimal. In addition, since flexible subcutaneous ICD 390 is implanted in a patient, the position of the at least one receiver antenna should be easily identifiable on the outer surface of the patient's skin such that the transmitter antenna can be placed as close of possible to location of the at least one receiver antenna implanted in the patient. Furthermore, physiological differences in patients, such as their level of body fat, may affect the distance between the receiver antenna or antennas in the implanted flexible subcutaneous IMD and the placement of the transmitter antenna on the patient's skin. An increase in body fat level will increase the distance between certain portions of the flexible subcutaneous IMD and the outer surface of the patient's skin depending on where in the body of the patient the IMD is implanted.

As shown in FIG. 5, the receiver antenna (or antennas) can be placed in a number of possible locations in flexible subcutaneous ICD 390. For example, the receiver antenna can be placed in transition unit 394A, as shown by a line 398A. The receiver antenna can also be placed in transition unit 394B, as shown by a line 398B. Such a receiver antenna configuration was shown above in FIGS. 3A and 3B. In a further embodiment, receiver antennas can be placed in both of plurality of transition units 394A and 394B. The receiver antenna can also be placed around elongated flexible plurality of units 392, as shown by a line 400. As shown, elongated flexible plurality of units 392 includes a plurality of outer units 402A, 402B, 402C and 402N. Plurality of outer units 402A, 402B and 402N are passive outer units in that even though they are made of metal, they are not used as active electrodes for transmitting an electrical shock to a patient. Outer unit 402C, as shown, is embodied as an active outer unit, since it can be used as an active electrode for transmitting an electrical shock to the patient. In another embodiment, the receiver antenna can be placed around any one of the plurality of outer units which is passive, such as outer units 402A, 402B or 402N. Such a receiver antenna configuration was shown above in FIGS. 4A and 4B. As explained below, the receiver antenna is not to be placed around an active outer unit such as outer unit 402C.

In general, the receiver antenna should be placed in the flexible subcutaneous IMD of the disclosed technique in a location where a patient's body fat level has a minimal influence on the distance between the implant position of the IMD and the outer surface of the patient's skin. For example, in the case of a flexible subcutaneous ICD according to the disclosed technique, a first lead is placed to the right or left side of the sternum of the patient, with the elongated flexible plurality of units trailing down into the patient's abdominal region and continuing laterally in a dorsal direction around the heart. An obese patient may have significantly more body fat in the abdominal region than a skinny patient such that if the receiver antenna is placed centrally in the elongated flexible plurality of units, the recharging efficiency of the flexible subcutaneous ICD in the obese patient may be seriously affected and compromised. Placing the receiver antenna in the transition unit closest to the first lead may avoid such a limitation as the area adjacent to the sternum does not store significant levels of body fat. Once implanted, the flexible subcutaneous ICD may be positioned such that the transition unit is located directly above the solar plexus, just below the sternum. The solar plexus is a location on the human body where there are no fat deposits regardless of the fat level of the patient. Thus, regardless of whether the patient is obese or skinny, the distance between the receiver antenna and the transmitter antenna will be kept to a minimum, the distance being merely a function of the thickness of the patient's skin and not of his or her body fat level. In addition, as the transition unit will be adjacent to the sternum, it will be easily located thus simplifying the placement of the transmitter antenna for efficient energy transfer. The receiver antenna can also be placed around one of the outer units adjacent to a transition unit, such as outer unit 402A, 402B or 402N. As mentioned above, body fat levels will be minimal around the area in the patient where those outer units are positioned and locating their position vis-à-vis the outer surface of the patient's skin will be relatively simple.

The receiver antenna should not be placed around an active outer unit, such as outer unit 402C, due to wireless conductivity issues. Prior art IMDs which have an active can may have a number of limitations regarding the placement of a wireless power receiver. An active can is usually hermetically sealed to prevent any bodily fluids from entering the can, however the can is also made from metal since it can act as an active electrode. If a receiver antenna is placed inside the active can, wireless conductivity of the receiver antenna may suffer significantly as the hermetically sealed active can functions as a Faraday cage, substantially blocking electromagnetic radiation from entering or exiting the active can. In addition, the transfer of energy between a transmitter antenna and the receiver antenna located in an active can may cause the can to heat up sufficiently to cause tissue damage around the active can. Furthermore, placement of the receiver antenna requires additional room in the active can, which might need to be designed to include more volume to accommodate the receiver antenna. If the receiver antenna is placed outside the active can to increase wireless conductivity, then the receiver antenna has to be made of a biocompatible material which won't be affected by tissue growth or contact with bodily fluids, or an additional part needs to be connected with the active can to house such a receiver antenna, thereby increasing the volume of such an IMD.

According to the disclosed technique, such limitations are avoided by placing the receiver antenna either in a transition unit or around a passive outer unit. The placement of the receiver antenna in a transition unit avoids the issue of wireless conductivity, since transition units are not made of metal and thus will not form Faraday cages. This placement also avoids the issue of significant heat increase around the IMD as the transition unit, which made be made from a polymer, is not as good a conductor as an active can made of metal. A transition unit will thus heat up less during wireless energy transfer, causing less potential damage to body tissue around the transition unit. The placement of the receiver antenna around a passive outer unit will not significantly affect wireless conductivity as passive outer units do not act as active electrodes and the receiver antenna is placed outside the metal outer unit, thus avoiding the issues of Faraday cages.

In general, the elongated thin shape of the IMD of the disclosed technique as well as the cylindrical configuration of the receiver antenna enables a wireless power receiver to be included in a flexible subcutaneous IMD without requiring any substantial increase in volume of such a device. Furthermore, since the flexible subcutaneous IMD of the disclosed technique includes non-electrically active parts, which once implanted, may be located relatively close to the outer surface of the skin and which do not form a Faraday cage, a wireless power receiver, including its antenna or antennas, can be placed in an effective, space-efficient location for maximizing the efficiency of wireless energy transfer while minimizing damage to surrounding tissue around the IMD. It is noted as well that in the case of ICDs, prior art intracardiac ICDs and prior art subcutaneous ICDs include a can or housing which as a whole is active. Unlike the disclosed technique, such prior art designs make it difficult if not impractical to place a receiver antenna around the outer surface of such a can or housing as such surfaces do not have non-active parts by design where a charging coil could be positioned close enough to the skin of a patient to be recharged wirelessly.

Reference is now made to FIG. 6, which is a schematic illustration showing the coupling between a receiver antenna and a rechargeable battery in a flexible subcutaneous IMD, generally referenced 420, constructed and operative in accordance with a further embodiment of the disclosed technique. As mentioned above, the disclosed technique relates to a flexible subcutaneous IMD, having a rechargeable battery as a power source. Energy from a wireless transmitter, as described below in FIG. 7, is received by a wireless receiver in the flexible subcutaneous IMD (not shown). The received energy is then used to recharge the rechargeable battery. FIG. 6 shows a receiver 421 which includes an antenna 422 and an interface 424. Antenna 422 can be any of the antenna configurations shown above in FIGS. 2A and 2B and positioned anywhere in the flexible subcutaneous IMD as described above in FIGS. 3A-4B. Antenna 422 can be embodied as a single antenna power receiver, a dual antenna power receiver or a multi-antennae power receiver (even though schematically it is shown as a single antenna). Antenna 422 is coupled with interface 424. Interface 424 may be situated in a transition unit (not shown) of the IMD, the elongated flexible plurality of units (not shown) of the IMD or can be embodied as part of the electronics (not shown) of the IMD. For example, interface 424 may be embodied as an inner component in the IMD, surrounded by an outer unit (not shown). Interface 424 is coupled with a battery 426 and substantially interfaces the energy transfer between antenna 422 and battery 426. Battery 426 may be a plurality of batteries. According to one embodiment of the disclosed technique, each antenna in the IMD may have a respective interface.

A wireless transmitter transmits electromagnetic radiation (not shown) in the direction of antenna 422. Antenna 422 receives the energy. The energy received may not be continuous, may come in spurts and may be received at a current and voltage which is not appropriate for battery 426. The energy received by antenna 422 is passed to interface 424. Interface 424 may include an energy container (not shown), such as a capacitor or a coil, for storing energy received from antenna 422. Interface 424 can provide the energy it stored or received to battery 426 to recharge it at a constant current and voltage. Interface 424 may be able to provide a pulse width modulated signal to recharge battery 426.

As interface 424 may be embodied as part of the electronics of the flexible subcutaneous IMD of the disclosed technique, interface 424 may be coupled with a processor (not shown) of the flexible subcutaneous IMD. Interface 424, the processor or both may be able to inspect the amount of energy received by antenna 422 and the amount of energy transferred to battery 426 by sampling the current, voltage or both, either received by antenna 422 or being received by battery 426. The results of the inspection can be used by the processor to determine if the recharging circuit between antenna 422 and battery 426 is operating normally. The results of the inspection can also be used to ensure that antenna 422 is properly and efficiently receiving energy from the wireless transmitter and if not, the processor can provide a message to the patient or the administering physician (not shown) that there is an issue with the recharging procedure of the IMD. As explained below in FIGS. 9A and 9B, the recharging procedure of the disclosed technique is a standalone procedure such that battery 426 can be recharged even if it is totally discharged.

Interface 424, the processor or both can also measure and determine the temperatures of battery 426 as it is recharging and of antenna 422 as it receives electromagnetic energy. The transfer of energy from the wireless transmitter to the wireless receiver can cause an endothermic reaction in antenna 422, battery 426 or both. An increase in temperature above a predefined threshold may be dangerous to the patient as the heat absorbed may cause tissue damage to body tissue (such as burning the tissue) in the vicinity of antenna 422, battery 426 or both. For example, if the temperature of antenna 422 or battery 426 goes above 40° C., the processor may send a signal to wireless transmitter to cease transmitting energy until the temperature of either antenna 422, battery 426 or both reduces to below 40° C.

According to another embodiment of the disclosed technique, receiver 421 may also include a communication unit (not shown). The communication unit can be embodied as a separate unit coupled with interface 424 or antenna 422 or may be embodied as a part of interface 424. In this embodiment of the disclosed technique, the energy transferred from the wireless transmitter to antenna 422 may also be data modulated. In this respect, as energy is transferred to antenna 422 to recharge battery 426, signals can simultaneously be sent to the processor of the flexible subcutaneous IMD to program it. Thus recharging and programming of the flexible subcutaneous IMD can occur simultaneously. The communication unit may be used for demodulating the received energy and extracting the modulated data within in and providing the data to the processor (not shown) of the flexible subcutaneous IMD. It is noted as well that if the energy transferred from the wireless transmitter to receiver 421 includes modulated data, then in one embodiment, the modulated data is to be sent encrypted over a unique and secure transmission channel, such that programming of the flexible subcutaneous IMD can solely be performed at a physician's clinic where the patient goes to recharge his or her IMD. Such a transmission channel is different than the transmission channel the IMD may use to transfer information to a patient's monitoring device, such as a smartphone.

Reference is now made to FIG. 7, which is a schematic illustration of a transmitter for transferring energy to a receiver antenna, generally referenced 440, constructed and operative in accordance with another embodiment of the disclosed technique. FIG. 7 shows a charger transmitter 442 for wirelessly transferring energy to the wireless power receiver located in an IMD of the disclosed technique, as described above in FIG. 6. Charger transmitter 442 includes a wire 444, a plurality of transmitting antennas 446A, 446B and 446C and a plurality of suction bulbs 448A, 448B and 448C. Wire 444 couples charger transmitter 442 to plurality of transmitting antennas 446A-446C. It is noted that charger transmitter 442 can include only one transmitting antenna (not shown). Plurality of transmitting antennas 446A-446C are each respectively coupled with plurality of suction bulbs 448A-448C. In another embodiment of the disclosed technique, plurality of transmitting antennas 446A-446C are embodied as temporary stickers which can be attached to the chest of a patient, similar to electrocardiogram, also known as ECG, electrodes which are attached to the chest of a patient during an electrocardiogram.

Charger transmitter 442 pulls electricity from an electrical outlet and generates energy which can be transmitted via plurality of transmitting antennas 446A-446C to a receiving antenna in the IMD of the disclosed technique. Charger transmitter 442 may include a display (not shown), such as a CRT display or LCD display, and a plurality of indicators (not shown), such as LED indicators, to provide messages and information to a technician and/or physician tending to the procedure of recharging the batteries (not shown) of the IMD of the disclosed technique. It is noted that in one embodiment of the disclosed technique, charger transmitter 442 may include a rechargeable battery (not shown) for itself. When charger transmitter 442 is plugged into an electrical outlet, part of the drawn electricity from the electrical outlet is used to charge the rechargeable battery. In this embodiment, charger transmitter 442 is portable and does not need to be coupled with an electrical outlet to recharge the rechargeable batteries of an IMD of the disclosed technique. Such an embodiment can be used in emergency situations where the IMD needs to be recharged and the patient in whom the IMD is implanted is not located in a place where there is electricity.

In charger transmitter 442, each one of plurality of transmitting antennas 446A-446C includes a separate driver (not shown). Each one of plurality of transmitting antennas 446A-446C may be controlled separately by charger transmitter 442 and may operate at separate frequencies. For example, transmitting antenna 446A may transfer energy at a first frequency $f_1$, transmitting antenna 446B may transfer energy at a second frequency $f_2$ and transmitting antenna 446C may transfer energy at a third frequency $f_3$. According to the disclosed technique, maximum energy transfer efficiency from plurality of transmitting antennas 446A-446C to the receiver antenna (not shown) in the IMD is achieved when there is no fixed relationship between $f_1$, $f_2$ and $f_3$ such that $f_1$-$f_3$ are independent of one another in the mathematical sense. The reason for this may be that energy carriers of each of the frequencies act together as a concentrated vector from charger transmitter 442 towards a receiving antenna (not shown). This can occur when there is no fixed relationship between $f_1$, $f_2$ and $f_3$ and can minimize electromagnetic interference as well as radio frequency interference coming from parasitic radiation sources (not shown) in the vicinity of charger transmitter 442.

It is noted that in one embodiment, the number of transmitting antennas in charger transmitter 442 may be equal to the number of receiver antennas in the IMD. Similar to the receiver antennas in the IMD, each one of plurality of transmitting antennas 446A-446C may be embodied as a flexible foil antenna, as shown above in FIG. 2A, or as a coil, as shown above in FIG. 2B.

As mentioned above, the recharging procedure may take about 1-2 hours to complete. For maximum recharging efficiency, plurality of transmitter antennas 446A-446C should be held in place once positioned on a patient for the duration of the recharging procedure. In one embodiment of the disclosed technique plurality of suction bulbs 448A-448C are used to create a suction and vacuum, thereby keeping plurality of transmitter antennas 446A-446C in place. In this embodiment, once a best position on the patient's body for achieving maximum recharging efficiency between the transmitting antennas and receiver antennas is determined, a gel (not shown) is placed on that best position and a pump (not shown) is used to create a suction for plurality of suction bulbs 448A-448C over that best position. According to another embodiment of the disclosed technique, an elastic sleeve or an elastic band (both not shown) can be used to position and hold in place plurality of transmitter antennas 446A-446C on the best position on the patient's body. This embodiment may not include plurality of suction bulbs 448A-448C. According to a further embodiment of the disclosed technique, sticky tape can be used to position and hold in place plurality of transmitter antennas 446A-446C. According to another embodiment of the disclosed technique where transmitter antennas 446A-446C are embodied as temporary stickers, once a best position on the patient's body is determined, transmitter antennas 446A-446C are simply attached to that best position, held in place by the temporary sticker of each of transmitter antennas 446A-446C.

Plurality of transmitter antennas 446A-446C may each be flexible in at least a horizontal and vertical direction. In this respect, the surface of each transmitter antenna may be conformed to the curvature of the patient's body over a best position for placing each transmitter antenna for achieving maximum recharging efficiency. This conforming may also be achieved by using the vacuum generated by plurality of suction bulbs 448A-448C.

In general, the flexible subcutaneous IMD of the disclosed technique can transmit signals wirelessly to provide information about the functioning of the IMD during regular use and during a recharging procedure. Since a recharging procedure involves charger transmitter 442 as well, the IMD and charger transmitter 442 may first need to be paired such that they can communicate with one another. For example, communication between charger transmitter 442 and the IMD may be encrypted by a personal key which is dynamic and can change each time a recharging procedure is conducted. This prevents other sources of electromagnetic radiation from interfering with the communication between charger transmitter 442 and the IMD. Charger transmitter 442 may include a wireless channel, for example a dedicated radio frequency (herein abbreviated RF) channel, for transmitting and receiving information from the IMD, such as the charge status of a battery (not shown) of the IMD, how much energy has been transferred, how much time has elapsed since the recharging procedure began, the temperature of the battery, the voltage and current of the battery, device programmable parameters such as the defibrillation threshold (herein abbreviated DFT), the amount of energy to be delivered, the voltage of an electric shock applied and the like. As mentioned above, information may be modulated in the energy transferred from charger transmitter 442 to the receiver (not shown) of the flexible subcutaneous IMD. In this embodiment, charger transmitter 442 may include a modulator (not shown) or processor (not shown) for modulating data over the electromagnetic radiation transferred to the receiver of the IMD for charging the rechargeable batteries of the IMD. In this embodiment, charger transmitter 442 may include two communication channels, one for transferring energy to charge the rechargeable batteries, including modulated data for programming the flexible subcutaneous IMD and another for transmitting and receiving status information about the recharging process. In this embodiment, charger transmitter 442 may also include an input (not shown), such as a touch screen, for selecting programmable features of the IMD. For example, charger transmitter 442 may include a local wireless channel, for example using short-wavelength ultra high frequency radio wave wireless technology standards such as BLUETOOTH® technology, for communicating information it receives from the IMD to external devices, such as a computer, smartphone, tablet and the like as well as an embedded data channel, such as a serial channel, for transferring energy to recharge the batteries of the IMD and to program it. In such an embodiment, charger transmitter 442 includes a translator (not shown) for converting information received from the wireless RF channel into either information that can be transmitter and received over a BLUETOOTH® channel, a serial channel or both. According to another embodiment of the disclosed technique, the IMD may include the translator, thus enabling the IMD to directly communicate information to a computer, smartphone, tablet and the like over a BLUETOOTH® channel or serial channel.

During the recharging procedure, messages may be transmitted and received between charger transmitter 442 and the IMD using a messaging protocol. As mentioned above, the IMD may provide various metrics to charger transmitter 442 such that the information provided can be seen by a tending physician. The metrics may include the charging current of the rechargeable battery, the current voltage of the rechargeable battery as well as in the internal temperature of different sections of the IMD. According to the disclosed technique, charger transmitter 442 can recharge the rechargeable battery of the IMD regardless of the charge level of the rechargeable battery. In the case that a patient comes to his tending physician for a recharging procedure in which his IMD is not fully discharged, charger transmitter 442 and the IMD may first establish that the IMD is functioning properly. Once established that no malfunctions are present in the IMD, charger transmitter 442 may send a start of charge message to the IMD, which will be responded to with an acknowledgement (herein abbreviated ACK) message from the IMD back to charger transmitter 442. In response, the recharging procedure as described above will begin. Once the rechargeable battery has been fully charged, the IMD may send a message back to charger transmitter 442 indicating that charging should end. Charger transmitter 442 receives the message and thus ceases providing energy to the IMD to recharge its rechargeable batteries.

In the case that a patient comes to his tending physician for a recharging procedure in which his IMD is fully discharged, charger transmitter 442 begins the recharging procedure once plurality of transmitter antennas 446A-446C have been properly positioned on the patient. A predetermined amount of time may be required to provide enough charge to the rechargeable batteries of the IMD before the processor of the IMD wakes up and can function and provides messages back to charger transmitter 442. The predetermined amount of time may be for example 5 minutes. After the predetermined amount of time, charger transmitter 442 may be expecting a message from the IMD confirming that the IMD is functioning properly and that charging can continue. If such a message is not received, then charger transmitter 442 may stop sending energy to the IMD and may provide a malfunction message to the tending physician indicating an issue with the IMD implanted in the patient.

Figure 8:
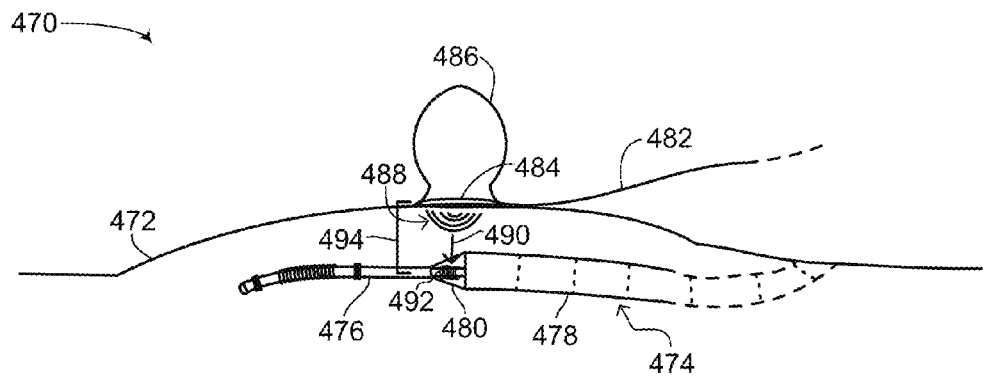
FIG. 8 is a schematic illustration showing the placement of a transmitter antenna on a patient over the position of the receiver antenna in a flexible subcutaneous IMD implanted in the patient, constructed and operative in accordance with a further embodiment of the disclosed technique.

Reference is now made to FIG. 8, which is a schematic illustration showing the placement of a transmitter antenna on a patient over the position of the receiver antenna in a flexible subcutaneous IMD implanted in the patient, generally referenced 470, constructed and operative in accordance with a further embodiment of the disclosed technique. FIG. 8 is a lateral cross-section view of a patient showing his torso 472. As shown a flexible subcutaneous ICD 474 of the disclosed technique is implanted subcutaneously in torso 472. Flexible subcutaneous ICD 474 includes a lead 476, an elongated flexible plurality of units 478 and a transition unit 480. Lead 476 and transition unit 480 are substantially placed over the right side or left side of the sternum (not shown) of the patient, while elongated flexible plurality of units 478 is positioned in the direction of the abdomen (not shown) of the patient, eventually looping around dorsally to the anterior side of the patient. Included in transition unit 480 is a receiver antenna 492 for receiving energy to be used for recharging a rechargeable battery (not shown) in elongated flexible plurality of units 478, programming flexible subcutaneous ICD 474 or both. Shown as well in FIG. 8 is a transmitter antenna 484, with a wire 482 coupling transmitter antenna 484 to a charger transmitter (not shown), for providing it with energy to be transmitted. A suction bulb 486 may be used to position transmitter antenna 484 on the surface of torso 474 and hold transmitter antenna 484 in place while energy is transferred from transmitter antenna 484 to receiver antenna 492. As mentioned above in FIG. 7, transmitter antenna 484 may be embodied without suction bulb 486 and may be a temporary sticker or patch which can be attached to the patient.

As shown in FIG. 8, transmitter antenna 484 transmits electromagnetic radiation 488 in the direction of receiver antenna 492. Electromagnetic radiation 488 is substantially a generated electromagnetic field. The efficiency of how much energy transmitter antenna 484 transmits and how much energy receiver antenna 492 receives is partly a function of the distance between the two, indicated by a line 494. The placement of flexible subcutaneous ICD 474 in the patient such that lead 476 and transition unit 480 sit in the area of the sternum, for example near the solar plexus (not shown), enables distance 494 to be kept to a minimum, thereby increasing the efficiency of energy transfer between transmitter antenna 484 and receiver antenna 492. The placement of flexible subcutaneous ICD 474 as shown also enables electromagnetic transparency such that a significant portion of electromagnetic radiation 488 reaches receiver antenna 492 and causes the generation of a charging current, i.e., energy received, which can be used to recharge the rechargeable batteries. The more efficient receiver antenna 492 is at absorbing and receiving electromagnetic radiation 488, the less electromagnetic radiation 488 will be absorbed by surrounding tissue around flexible subcutaneous ICD 474, in particular body tissue around transition unit 480 where receiver antenna 492 is situated. A high efficiency is required by receiver antenna 492 to avoid the body tissue around transition unit 480 from increasing in temperature by a number of degrees, since this may cause burning of such tissue. As described above in FIGS. 2A and 2B, the geometrical shape of receiver antenna 492 as well as its close placement to transmitter antenna 484 enables this high efficiency in transferring energy.

Electromagnetic radiation 488 is an electromagnetic field spanning a large spectrum of frequencies, such as 30-1500 kilohertz. As such, the energy transmitted by transmitter antenna 484 does not have a particular carrier frequency. In addition, to increase the transmission efficiency, more than one transmitter antenna (not shown in FIG. 8 but shown in FIGS. 7 and 9) may be used simultaneously to provide electromagnetic radiation. Also, each transmitter antenna may be embodied as a plurality of antennas and thus each plurality of transmitter antennas can generate a vectored beam of energy for each transmitter antenna to transmit. During a recharging procedure, electromagnetic radiation 488 may be transmitted continuously or in a pulsed manner, whereby energy is transmitted for a certain period of time, followed by a rest period when no energy is transmitted and then energy is transmitted once again, and so on. An interface (not shown), as described above in FIG. 6, along with a processor (not shown) in flexible subcutaneous ICD 474, may monitor and determine the efficiency of energy received by receiver antenna 492. If the determined efficiency is below a predefined threshold, then the bandwidth of frequencies of electromagnetic radiation 488, within the large spectrum mentioned above, may be altered in an attempt to find a bandwidth whereby the efficiency of receiver antenna 492 is increased. As shown above in FIG. 7, the wireless power transmitter of the disclosed technique may include a plurality of transmitter antennas, thus various frequency bandwidths can be attempted, one per transmitter antenna, in order to increase the efficiency of receiver antenna 492.

Besides transmitting energy for recharging the rechargeable battery of flexible subcutaneous ICD 474, communication between flexible subcutaneous ICD 474 and a charger transmitter (not shown) during a recharging procedure is achieved by wireless communication techniques as mentioned above. Communication in this regards includes messages sent between flexible subcutaneous ICD 474 and the charger transmitter as well as metric data sent from flexible subcutaneous ICD 474 to the charger transmitter. In one embodiment of the disclosed technique, a dedicated, separate RF channel (i.e., separate from energy transfer for recharging the rechargeable battery) is used for communication between flexible subcutaneous ICD 474 and the charger transmitter. In this embodiment, flexible subcutaneous ICD 474 may include an additional antenna (not shown), the charger transmitter may include an additional antenna (not shown) or both flexible subcutaneous ICD 474 and the charger transmitter may each include an additional antenna (not shown). The additional antenna in flexible subcutaneous ICD 474 may be placed in transition unit 480, elongated flexible plurality of units 478 or within lead 476. The additional antenna in the charger transmitter may be embodied as an additional transmitter antenna, similar to transmitter antenna 484. RF signals transmitted over the additional antenna or antennas may be transmitted using a secure key or using frequency-shift keying. In another embodiment of the disclosed technique, communication between flexible subcutaneous ICD 474 and the charger transmitter occurs between transmitter antenna 484 and receiver antenna 492. In this embodiment, no additional antennas are required. In this embodiment, communication signals are modulated at a higher frequency in comparison to the signals used to transfer energy. For example, the communication signals may be modulated in the kilohertz (herein abbreviated kHz) range, such as from 30 kHz-200 kHz. In this embodiment, the communication signals are embedded in the energy transfer signals between transmitter antenna 484 and receiver antenna 492. Also, the communication signals in this embodiment do not need to be encrypted with a secure key.

It is noted that the methods of wireless energy transfer described herein have been related to electromagnetic radiation. However the disclosed technique is not limited only to wireless electrical charging. According to other embodiments of the disclosed technique, acoustic energy, such as ultrasound, and mechanical methods for generating energy can also be used with the disclosed technique for wirelessly transferring energy to the flexible subcutaneous IMD of the disclosed technique for charging a rechargeable battery therein. In such embodiments (not shown), the charger transmitter generates acoustic energy or mechanical energy, the transmitter antenna is thus an antenna for transmitting the generated acoustic or mechanical energy towards the body of a patient and the receiver antenna is thus an antenna to receive the generated acoustic or mechanical energy. The received energy is then used to charge the rechargeable battery of the IMD. In these embodiments, the IMD of the disclosed technique may include a converter unit (not shown) for converting the received acoustic or mechanical energy into a form of energy that can be used to charge the rechargeable battery of the IMD.

Figure 9A:
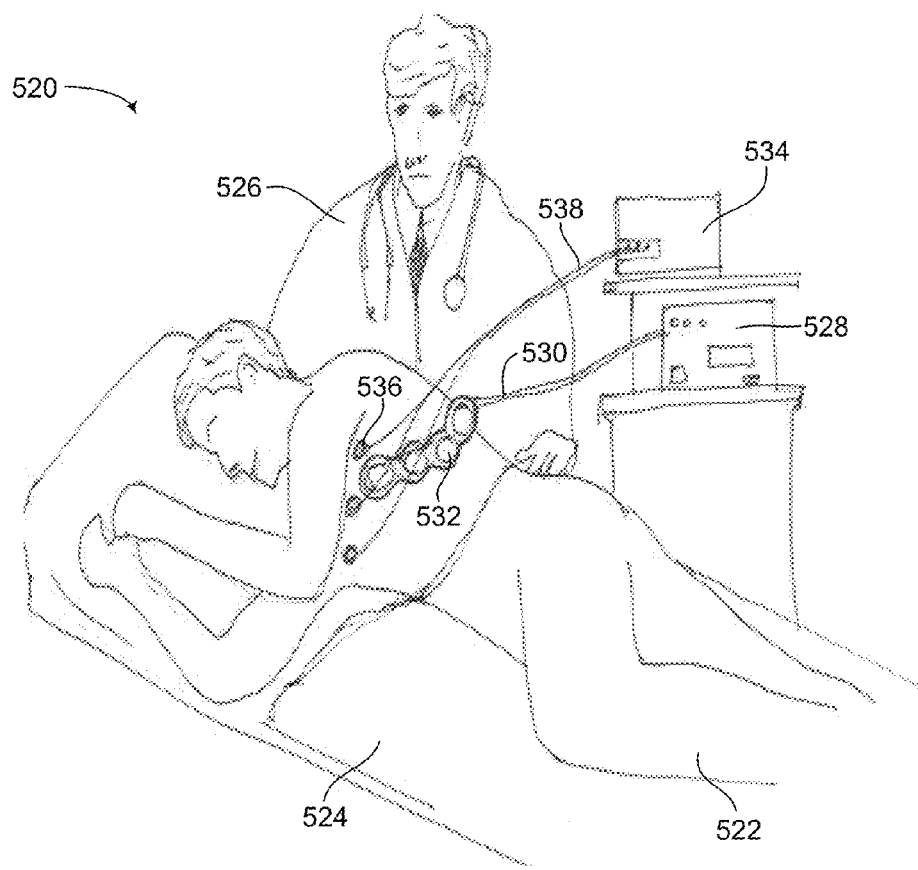
FIG. 9A is a schematic illustration of a first charging session at a physician's clinic for recharging the rechargeable battery of a flexible subcutaneous IMD, constructed and operative in accordance with another embodiment of the disclosed technique.

Reference is now made to FIG. 9A, which is a schematic illustration of a first charging session at a physician's clinic for recharging the rechargeable battery of a flexible subcutaneous IMD, generally referenced 520, constructed and operative in accordance with another embodiment of the disclosed technique. As shown, a patient 522 with an implanted flexible subcutaneous IMD of the disclosed technique (not shown) has come to a clinic of his tending physician 526 for either a routine check-up on the functioning of his IMD or explicitly for recharging the IMD. In order to ease placement of the transmitter antennas for recharging the IMD, patient 522 may lie on his side on an examining table 524. Shown in FIG. 9A is also a charger transmitter 528, which is substantially similar to charger transmitter 442 (FIG. 7). Like the charger transmitter described above, charger transmitter 528 includes a wire 530 as well as a plurality of suction bulbs 532. Each one of plurality of suction bulbs 532 includes a transmitter antenna (not shown). Tending physician 526 determines a best position for plurality of suction bulbs 532 on the skin of patient 522, by determining an approximate position of the receiver antenna (not show) or receiver antennas (not shown) in the IMD under the skin of patient 522. Plurality of suction bulbs 532 are then used to hold the transmitter antennas in place on the skin of patient 522. While charger transmitter 528 charges the IMD, patient 522 may also be hooked up to an external electrocardiogram (herein abbreviated ECG) monitor 534, which includes a plurality of patches 536, each coupled with ECG monitor 534 via a cable 538. ECG monitor 534 is used to monitor the cardiac activity of the heart of patient 522 while his IMD charges.

As mentioned above, a patient with an IMD of the disclosed technique may be requested to check-in with his physician once every couple of months or once every year and every time the IMD delivers electrical shocks to treat a detected arrhythmia. At each check-up, physician 526 may check the charge level of the rechargeable batteries of the IMD and decide if the IMD should be charged or not. For example, a charge level of 50% or less for the rechargeable battery of the IMD may be an indication to physician 526 that the IMD should be recharged. It is noted that the IMD may include wireless communication capabilities, such as via the BLUETOOTH® protocol, low energy BLUETOOTH® (also known as BLE) protocol, RF-based, ultrasound-based and infrared-based communication. At the clinic, the IMD may provide information wirelessly to physician 526 about the status of the IMD, including the amount of charge left in the IMD. Recall that even if the IMD has only 50% charge left, it may still work for another year and can provide up to ten high voltage electrical shocks. The IMD may also provide information wirelessly to charger transmitter 528 which can then display the information to physician 526.

It is noted that in another embodiment of the disclosed technique, the charging session may be performed while the patient is seated in a chair. In such an embodiment, plurality of suction bulbs 532 may be replaced by a plurality of temporary stickers or patches (both not shown) which can be placed directly on the patient's chest. Each sticker or patch may include a transmitter antenna (not shown). This is shown in greater detail below in FIG. 9B.

Shown in FIG. 9A is a recharging procedure. During the recharging procedure, tending physician 526 may receive information about the status of the IMD either via charger transmitter 528 or via the IMD itself. Information may include the current charge level of the IMD, the current and voltage of the rechargeable batteries, the internal temperature of various sections of the IMD and the like. According to one embodiment of the disclosed technique, once charger transmitter 528 sends a recharge procedure signal to the IMD, the IMD is switched to a charging mode in which its sensing capabilities are disabled. In the charging mode, the IMD cannot detect arrhythmias. In this embodiment, tending physician 526 uses ECG monitor 534 to monitor patient 522 for arrhythmias. If tending physician 526 detects an arrhythmia in patient 522, then a high voltage electric shock can be delivered to patient 522 manually via tending physician 526 using an external defibrillator (not shown). In another embodiment, charger transmitter 528 may include an override button (not shown) which can stop the recharging procedure and send a signal to the IMD to deliver a high voltage electric shock to patient 522. The override button may also function to re-enable the sensing capabilities of the IMD. According to another embodiment, when charger transmitter 528 sends a recharge procedure signal to the IMD, the IMD continues to function normally, including monitoring the heart of patient 522 for detecting arrhythmias and providing high voltage electric shocks to patient 522 if arrhythmias are detected.

Figure 9B:
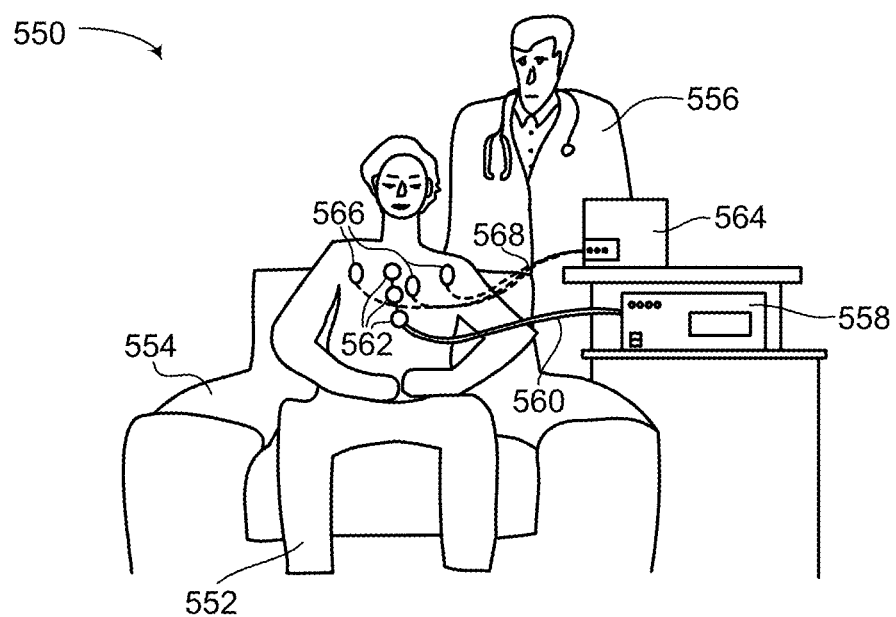
FIG. 9B is a schematic illustration of a second charging session at a physician's clinic for recharging the rechargeable battery of a flexible subcutaneous IMD, constructed and operative in accordance with a further embodiment of the disclosed technique.

Reference is now made to FIG. 9B, which is a schematic illustration of a second charging session at a physician's clinic for recharging the rechargeable battery of a flexible subcutaneous IMD, generally referenced 550, constructed and operative in accordance with a further embodiment of the disclosed technique. As shown, a patient 552 with an implanted flexible subcutaneous IMD of the disclosed technique (not shown) has come to a clinic of his tending physician 556 for either a routine check-up on the functioning of his IMD or explicitly for recharging the IMD. In this embodiment, patient 552 is sitting in a comfortable chair 554 and recharging of his IMD can occur in a seated position. Shown in FIG. 9B is also a charger transmitter 558, which is substantially similar to charger transmitter 528 (FIG. 9A). Charger transmitter 558 includes a wire 560, however instead of a plurality of suction bulbs it includes a plurality of patches 562. Plurality of patches 562 may be stickers and can be attached to the body of patient 552 in a manner similar to how ECG electrodes are attached to a patient. Each one of plurality of patches 562 includes a transmitter antenna (not shown). Tending physician 556 determines a best position for plurality of patches 562 on the skin of patient 552, by determining an approximate position of the receiver antenna (not show) or receiver antennas (not shown) in the IMD under the skin of patient 552. While charger transmitter 558 charges the IMD, patient 552 may also be hooked up to an external ECG monitor 564, which includes a plurality of electrodes 566, each coupled with ECG monitor 564 via a cable 568. ECG monitor 564 is used to monitor the cardiac activity of the heart of patient 552 while his IMD charges. The recharging procedure shown in FIG. 9B is similar to the recharging procedure described above in FIG. 9A.

It will be appreciated by persons skilled in the art that the disclosed technique is not limited to what has been particularly shown and described hereinabove. Rather the scope of the disclosed technique is defined only by the claims, which follow.

The invention claimed is:

1. Flexible subcutaneous implantable medical device (IMD), comprising:
    an elongated and flexible body;
    a plurality of electronic components;
    at least one rechargeable battery, for powering said plurality of electronic components;
    at least one antenna, for receiving and transmitting electromagnetic radiation;
    at least one lead, for providing an electric shock; and
    at least one transition unit, for coupling said at least one lead to at least one end of said elongated and flexible body,
    wherein said elongated and flexible body is structured from a plurality of units;
    wherein a first one of said plurality of units encapsulates said at least one rechargeable battery;
    wherein each one of said other plurality of units respectively encapsulates a respective one of said plurality of electronic components;
    wherein said at least one antenna is positioned in said at least one transition unit;
    wherein said at least one transition unit is covered with a biocompatible polymer;
    wherein said at least one antenna receives electromagnetic radiation for recharging said at least one rechargeable battery; and
    wherein said at least one antenna comprises a copper coil having a generally cylindrical shape.

2. The flexible subcutaneous IMD according to claim 1, wherein a first one of said at least one antenna is coupled with a second one of said at least one antenna in series.

3. The flexible subcutaneous IMD according to claim 2, wherein said first one of said at least one antenna is coupled with said second one of said at least one antenna using a coupler.

4. The flexible subcutaneous IMD according to claim 3, wherein said coupler is selected from the list consisting of:
    a semi-circular shaped coupler;
    a 'C'-shaped coupler; and
    a 'U'-shaped coupler.

5. The flexible subcutaneous IMD according to claim 1, further comprising:
    a dielectric feed through, coupled with said at least one lead, for enabling electrical coupling between said elongated and flexible body and said at least one transition unit, and said at least one lead while not compromising a hermetic seal on said elongated and flexible body; and
    a bus, for coupling said at least one antenna with said dielectric feed through, for enabling said received electromagnetic radiation to be transferred electrically into said elongated and flexible body.

6. The flexible subcutaneous IMD according to claim 1, wherein said at least one transition unit is made from a polymer, thereby minimizing heat increases when said electromagnetic radiation is received for recharging said at least one rechargeable battery.

7. The flexible subcutaneous IMD according to claim 1, further comprising at least one interface, coupled between said at least one antenna and said at least one rechargeable battery, for interfacing an energy transfer of said received electromagnetic radiation between said at least one antenna and said at least one rechargeable battery.

8. The flexible subcutaneous IMD according to claim 7, wherein said at least one interface is placed in a position selected from the list consisting of:
    in said at least one transition unit; and
    in said plurality of units.

9. The flexible subcutaneous IMD according to claim 7, wherein said at least one interface is embodied as part of said plurality of electronic components.

10. The flexible subcutaneous IMD according to claim 7, wherein each one of said at least one antenna is coupled with a respective one of said at least one interface.

11. The flexible subcutaneous IMD according to claim 7, said at least one interface comprising an energy container for storing said received electromagnetic radiation from said at least one antenna.

12. The flexible subcutaneous IMD according to claim 11, wherein said interfacing comprises providing said stored received electromagnetic radiation at a constant current and voltage to said at least one rechargeable battery.

13. The flexible subcutaneous IMD according to claim 7, wherein said energy container is selected from the list consisting of:
   a capacitor; and
   a coil.

14. The flexible subcutaneous IMD according to claim 7, wherein said interfacing comprises providing said received electromagnetic radiation as a pulse width modulated signal for recharging said at least one rechargeable battery.

15. The flexible subcutaneous IMD according to claim 7, wherein said interfacing comprises sampling at least one of a current and a voltage of said received electromagnetic radiation for ensuring proper recharging of said at least one rechargeable battery.

16. The flexible subcutaneous IMD according to claim 7, wherein said interfacing comprises determining a temperature of at least one of said at least one antenna and said at least one rechargeable battery.

17. The flexible subcutaneous IMD according to claim 7, said at least one interface comprising a communication unit, for demodulating said received electromagnetic radiation and extracting modulated data within said received electromagnetic radiation.

18. The flexible subcutaneous IMD according to claim 1, said at least one antenna comprising a copper coil, wherein said copper coil is wound around a hollow ferrite core, thereby giving said copper coil a generally cylindrical shape.

19. The flexible subcutaneous IMD according to claim 18, wherein said generally cylindrical shape enables said copper coil to conform to a shape of said flexible subcutaneous IMD.

20. The flexible subcutaneous IMD according to claim 18, wherein said generally cylindrical shape enables said copper coil to be omnidirectional for receiving said electromagnetic radiation.

21. Flexible subcutaneous implantable medical device (IMD), comprising:
   an elongated and flexible body;
   a plurality of electronic components;
   at least one rechargeable battery, for powering said plurality of electronic components;
   at least one antenna, for receiving and transmitting electromagnetic radiation; and
   at least one lead, for providing an electric shock,
   wherein said at least one lead terminates at least one end of said elongated and flexible body;
   wherein said elongated and flexible body is structured from a plurality of units;
   wherein a first one of said plurality of units encapsulates said at least one rechargeable battery;
   wherein each one of said other plurality of units respectively encapsulates a respective one of said plurality of electronic components;
   wherein at least one of said plurality of units may be electrically active;
   wherein said at least one antenna is positioned around at least one of said plurality of units which is not electrically active;
   wherein said at least one antenna is covered with a biocompatible polymer; and
   wherein said at least one antenna receives electromagnetic radiation for recharging said at least one rechargeable battery.

* * * * *